(12) United States Patent
Zhang et al.

(10) Patent No.: US 10,549,097 B2
(45) Date of Patent: Feb. 4, 2020

(54) SYSTEMS AND METHODS FOR SPATIALLY SELECTIVE SPINAL CORD STIMULATION

(71) Applicant: Boston Scientific Neuromodulation Corporation, Valencia, CA (US)

(72) Inventors: Tianhe Zhang, Studio City, CA (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 193 days.

(21) Appl. No.: 15/684,196

(22) Filed: Aug. 23, 2017

(65) Prior Publication Data

US 2018/0056068 A1    Mar. 1, 2018

Related U.S. Application Data

(60) Provisional application No. 62/379,098, filed on Aug. 24, 2016.

(51) Int. Cl.
*A61N 1/36* (2006.01)
*A61N 1/05* (2006.01)
*A61N 1/372* (2006.01)

(52) U.S. Cl.
CPC ....... *A61N 1/36062* (2017.08); *A61N 1/0551* (2013.01); *A61N 1/0553* (2013.01);
(Continued)

(58) Field of Classification Search
CPC .............. A61N 1/36062; A61N 1/0551; A61N 1/0553; A61N 1/36071; A61N 1/36185; A61N 1/36189; A61N 1/37247
(Continued)

(56) References Cited

U.S. PATENT DOCUMENTS

| 8,412,345 B2 | 4/2013 | Moffitt |
| 8,909,350 B2 | 12/2014 | Lee |

(Continued)

FOREIGN PATENT DOCUMENTS

| WO | WO-2010028084 A2 | 3/2010 |
| WO | WO-2018039296 A2 | 3/2018 |
| WO | WO-2018039296 A3 | 3/2018 |

OTHER PUBLICATIONS

Al-Kaisy, Adnan, et al., "Sustained Effectiveness of 10 kHz High-Frequency Spinal Cord Stimulation for Patients with Chronic, Low Back Pain: 24-Month Results of a Prospective Multicenter Study", Pain Medicine 2014; 15, (2014), 347-354.

(Continued)

*Primary Examiner* — Carl H Layno
*Assistant Examiner* — Erin M Piateski
(74) *Attorney, Agent, or Firm* — Schwegman Lundberg & Woessner, P.A.

(57) ABSTRACT

A system may include electrodes on at least one lead configured to be operationally positioned for use in modulating a volume of neural tissue, a neural modulation generator configured to deliver energy using at least some electrodes to modulate the volume of neural tissue, a programming system configured to program the programmed modulation parameter set, including determine electrode fractionalizations for the electrodes based on a target multipole. The programmed parameter set may include the determined electrode fractionalizations. The target multipole may be used to determine electrode fractionalizations having at least three target poles that directionally and progressively stack fractionalizations of target poles to provide a linear electric field over the volume of tissue. The neural modulation generator may be configured to use the programmed (Continued)

modulation parameter set to provide the linear electric field over the volume of tissue.

20 Claims, 21 Drawing Sheets

(52) U.S. Cl.
CPC ..... *A61N 1/36071* (2013.01); *A61N 1/36185* (2013.01); *A61N 1/36189* (2013.01); *A61N 1/37247* (2013.01)

(58) Field of Classification Search
USPC .......................................................... 607/46
See application file for complete search history.

(56) References Cited

U.S. PATENT DOCUMENTS

| | | | |
|---|---|---|---|
| 9,044,610 B2 | 6/2015 | Rosenberg et al. | |
| 2009/0287271 A1* | 11/2009 | Blum | A61N 1/37247 607/45 |
| 2011/0022114 A1 | 1/2011 | Navarro et al. | |
| 2012/0239115 A1* | 9/2012 | Lee | A61N 1/36185 607/59 |
| 2012/0296396 A1* | 11/2012 | Moffitt | G16H 40/63 607/59 |
| 2013/0204327 A1* | 8/2013 | Carlton | A61N 1/37235 607/59 |
| 2013/0253610 A1* | 9/2013 | Lee | A61N 1/36185 607/59 |
| 2014/0100631 A1* | 4/2014 | Rao | A61N 1/36185 607/59 |
| 2015/0073502 A1 | 3/2015 | Lee et al. | |
| 2016/0082261 A1 | 3/2016 | Moffitt et al. | |

OTHER PUBLICATIONS

Alo, Kenneth, et al., "New Trends in Neuromodulation for the Management of Neuropathic Pain", Neurosurgery, vol. 50, No. 4, (Apr. 2002), 690-704.

Gustafsson, Bengt, et al., "Direct and Indirect Activation of Nerve Cells by Electrical Pulses Applied Extracellularly", J. Physiol. 258, pp. 33-61 (1976).

Reilly, J. Patrick, et al., "Sensory Effects of Transient Electrical Stimulation—Evaluation with a Neuroelectric Model", IEEE Transactions on Biomedical Engineering, vol. BME-32, No. 12, (Dec. 1985), 1001-1011.

Szucs, Peter, et al., "Axon Diversity of Lamina I Local-Circuit Neurons in the Lumbar Spinal Cord", The Journal of Comparative Neurology | Research in Systems Neuroscience 521, (2013), 2719-2741.

"Australian Application Serial No. 2017316684, First Examination Report dated Jun. 19, 2019", 4 pgs.

"International Application Serial No. PCT/US2017/048125, International Preliminary Report on Patentability dated Mar. 7, 2019", 11 pgs.

"International Application Serial No. PCT/US2017/048125, International Search Report dated Feb. 9, 2018", 8 pgs.

"International Application Serial No. PCT/US2017/048125, Invitation to Pay Add'l Fees and Partial Search Report dated Dec. 5, 2017", 15 pgs.

"International Application Serial No. PCT/US2017/048125, Written Opinion dated Feb. 9, 2018", 11 pgs.

* cited by examiner

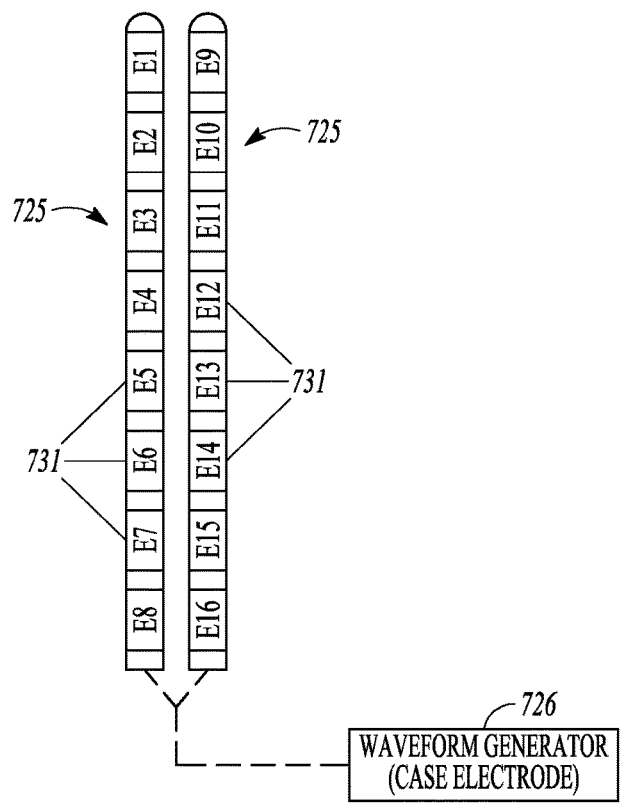
FIG. 7
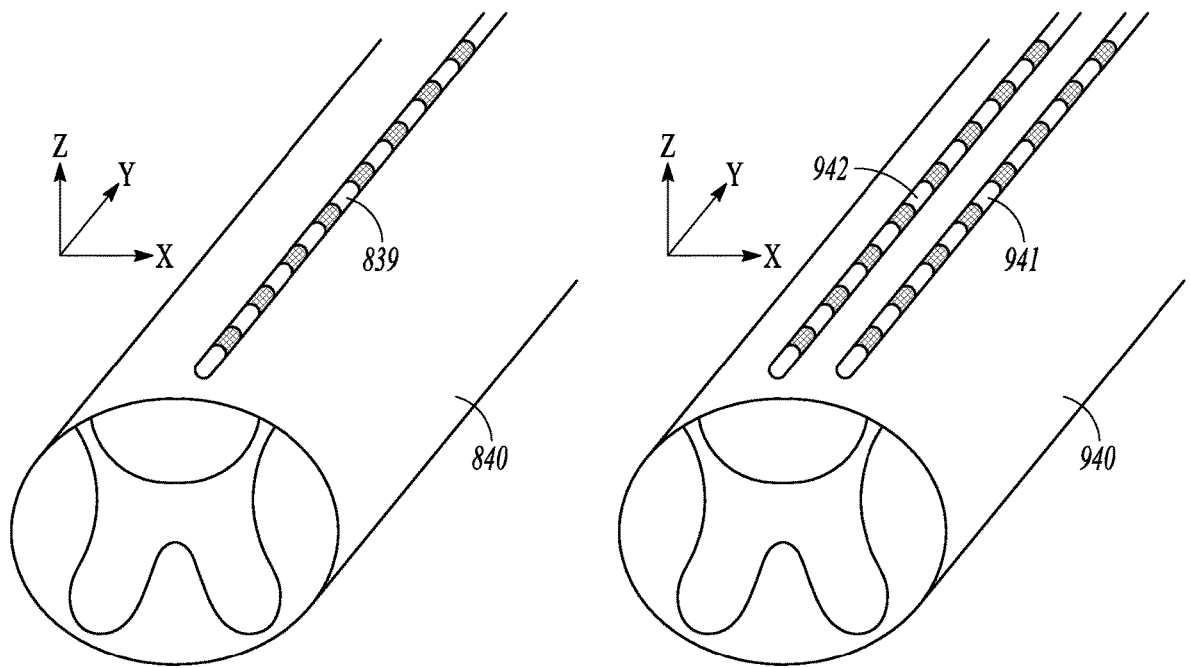
FIG. 8                    FIG. 9

Ex = dV/dx

TRANSFER MATRIX A (m x n)

$$\begin{bmatrix} m \text{ field potential values due to constituent source \#1} & m \text{ field potential values due to constituent source \#2} & m \text{ field potential values due to constituent source \#3} & \cdots & m \text{ field potential values due to constituent source \#n} \end{bmatrix}$$

*FIG. 20*

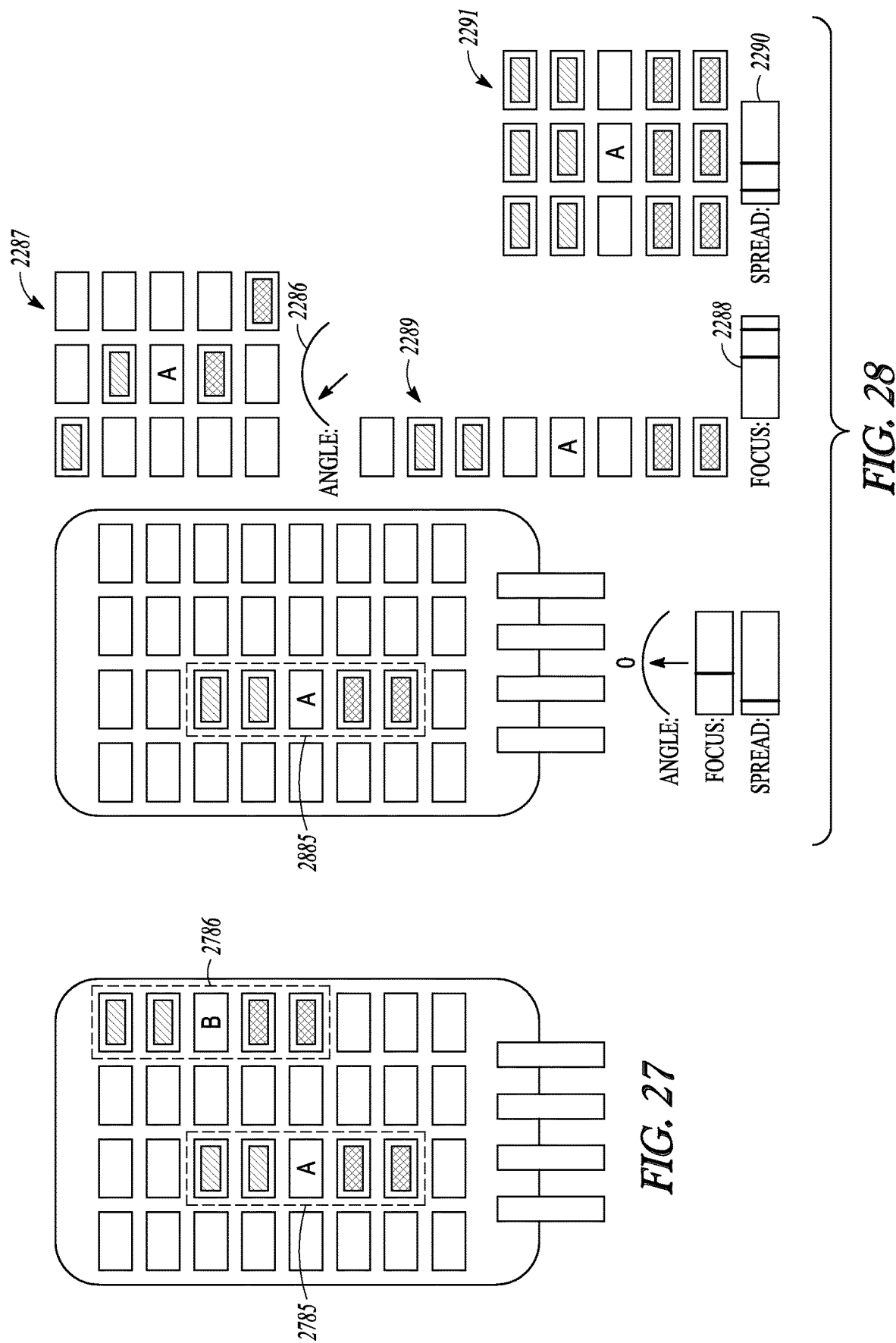

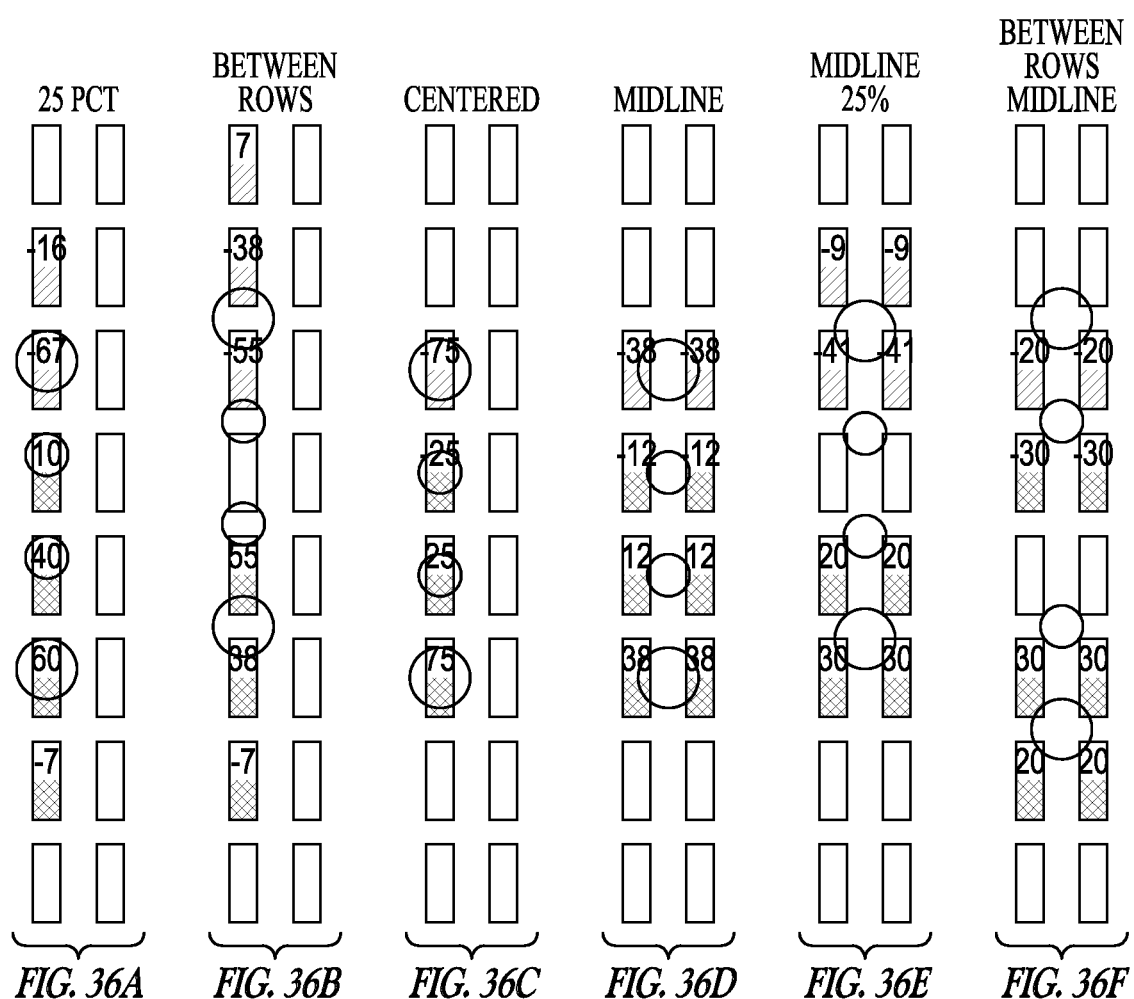

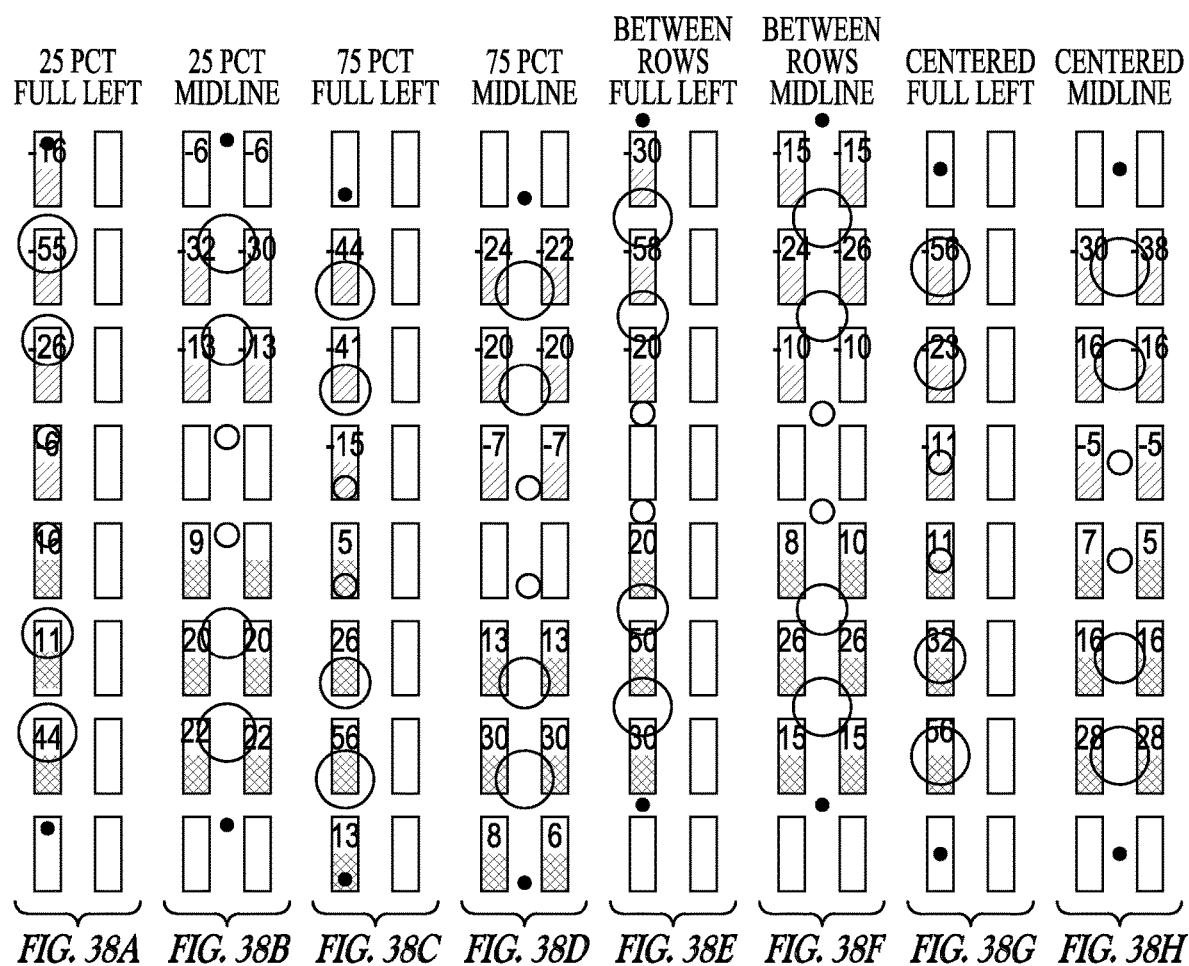

SYSTEMS AND METHODS FOR SPATIALLY SELECTIVE SPINAL CORD STIMULATION

CLAIM OF PRIORITY

This application claims the benefit of priority under 35 U.S.C. § 119(e) of U.S. Provisional Patent Application Ser. No. 62/379,098, filed on Aug. 24, 2016, which is herein incorporated by reference in its entirety.

TECHNICAL FIELD

This document relates generally to medical devices, and more particularly, to systems, devices and methods for delivering neural modulation.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. Some neural targets may be complex structures with different types of nerve fibers. An example of such a complex structure is the neuronal elements in and around the spinal cord targeted by SCS.

SUMMARY

An example (e.g. "Example 1") of a system may include electrodes on at least one lead configured to be operationally positioned for use in modulating a volume of neural tissue, a neural modulation generator configured to deliver energy using at least some electrodes to modulate the volume of neural tissue, a programming system configured to program the programmed modulation parameter set, including determine electrode fractionalizations for the electrodes based on a target multipole. The programmed parameter set may include the determined electrode fractionalizations. The target multipole may be used to determine electrode fractionalizations having at least three target poles that directionally and progressively stack fractionalizations of target poles to provide a linear electric field over the volume of tissue. The neural modulation generator may be configured to use the programmed modulation parameter set to provide the linear electric field over the volume of tissue. Thus, by way of example and not limitation, a user may control the properties of the linear field to minimize or maximize the field in a specific direction.

In Example 2, the subject matter of Example 1 may optionally be configured such that the target multipole includes a center (or other point), at least a first target anode and a second target anode on an anodic side of the center (or other point) of the target multipole, and at least a first target cathode and a second target cathode on an opposing cathodic side of the center (or other point) of the target multipole. There may be more than one anode and more than one cathode as necessary based on the user-defined length of the multipole and/or the inverse calculation. Fractionalizations may be determined using knowledge of the pole(s) and the span of the multipole.

In Example 3, the subject matter of Example 2 may optionally be configured such that the first and second target anodes, the center, and the first and second target cathodes are in-line with each other.

In Example 4, the subject matter of any one or any combination of Examples 1-3 may optionally be configured such that at least some of the electrodes on the lead include directional electrodes that extend less than 360 degrees around a circumference of the lead.

In Example 5, the subject matter of Example 1 may optionally be configured such that the target multipole, which directionally and progressively stacks fractionalizations of target poles, includes a center, a first target anode separated from the center, and a second target anode separated from the first target anode. The second target anode may be further away from the center than the first target anode and the second target anode may have a higher fractionalization percentage then the first target anode. The first target cathode may be separated from the center, and a second target cathode separated from the first target cathode. The second target cathode may be further away from the center than the first target cathode and the second target cathode may have a higher fractionalization percentage then the first target cathode. This may be extended to more than three anodes, to more than three cathodes, and to situations where the fractionalization of any given polarity within the multipole does not add up to 100%.

In Example 6, the subject matter of Example 5 may optionally be configured such that the system further comprises a flanking target anode separated from the second target anode where the flanking target anode is further away from the center than the second target anode, and a flanking target cathode separated from the second target cathode where the flanking target cathode is further away from the center than the second target cathode.

In Example 7, the subject matter of any one or any combination of Examples 5-6 may optionally be configured such that the system further comprises flanking electrodes on opposing sides of the first target anode and having opposite polarity to the first target anode, flanking electrodes on opposing sides of the second target anode and having opposite polarity to the second target anode, flanking electrodes on opposing side of the first target cathode and having opposite polarity to the first target cathode, and flanking electrodes on opposing sides of the second target cathode and having opposite polarity to the second target cathode.

In Example 8, the subject matter of Example 2 may optionally be configured such that the system further comprises a third target anode on the anodic side of the center of the target multipole and a third target cathode on the cathodic side of the center of the target multipole.

In Example 9, the subject matter of Example 2 may optionally be configured such that the target multipole further comprises a flanking target anode on the anodic side of the center, and a flanking target cathode on the cathodic side of the center, wherein the first, second and flanking target anodes, the center, and the first, second and flanking target cathodes are in-line with each other.

In Example 10, the subject matter of any one or any combination of Examples 1-9 may optionally be configured such that the programming system includes a user interface configured to receive at least one user input selected from the group of user inputs consisting of: a user input to adjust an angle of an axis of linear progression for the target multipole; a user input to adjust a focus of the target multipole to change a length of the linear electric field; and a user input to adjust a spread of the target multipole to change a width of the linear electric field.

In Example 11, the subject matter of any one or any combination of Examples 1-10 may optionally be configured such that the programming system may be configured to receive as a user input a user-drawn region on an anatomical representation, and automatically determine the target multipole based on the user input, the target multipole being used to determine the electrode fractionalizations for the plurality of electrodes.

In Example 12, the subject matter of any one or any combination of Examples 1-11 may optionally be configured such that the programming system may be configured to receive as a user input a user-identified patient pain area, and automatically determine the target multipole based on the user input, the target multipole being used to determine the electrode fractionalizations for the plurality of electrodes.

In Example 13, the subject matter of any one or any combination of Examples 1-12 may optionally be configured such that the programming system may be configured to display a gradient control element, receive a user input to adjust the gradient control element, and adjust a strength of a therapy based on the adjusted gradient control element.

In Example 14, the subject matter of any one or any combination of Examples 1-13 may optionally be configured such that the neural modulation generator may be programmed to automatically move the target multipole within an array of electrodes.

In Example 15, the subject matter of any one or any combination of Examples 1-14 may optionally be configured such that the programming system may be configured to implement a search heuristic to optimize a distance and amplitude on each pole in the target multipole to maximize an absolute value of the electric field, and to optimize for a number of poles in the target multipole, orientation angle of the electric field, focus of the electric field, and spread of the electric field.

An example (e.g. "Example 16") of a method for modulating a volume of tissue using a plurality of electrodes may include programming a modulation parameter set, including determining the electrode fractionalizations for the plurality of electrodes based on a target multipole. The programmed parameter set may include the determined electrode fractionalizations. The target multipole may have at least three target poles that directionally and progressively stacks fractionalizations of target poles to provide a linear electric field over the volume of tissue. The method may further include delivering energy using the active physical electrodes and the programmed parameter set to provide the linear electric field.

In Example 17, the subject matter of Example 16 may optionally be configured such that the target multipole includes a center, a first target anode and a second target anode on an anodic side of the center of the target multipole, and a first target cathode and a second target cathode on an opposing cathodic side of the center of the target multipole.

In Example 18, the subject matter of Example 17 may optionally be configured such that the target multipole may further comprise a flanking target anode on the anodic side of the center, and a flanking target cathode on the cathodic side of the center, wherein the first, second and flanking target anodes, the center, and the first, second and flanking target cathodes are in-line.

In Example 19, the subject matter of any one or any combination of Examples 16-18 may optionally be configured such that the at least three target poles are in-line with each other.

In Example 20, the subject matter of Example 19 may optionally be configured such that the first target anode and the first target cathode may have equal magnitudes, and the second target anode and second target cathode may have equal magnitudes.

In Example 21, the subject matter of Example 20 may optionally be configured such that distances from the first target anode to the center and from the first target cathode to the center are equal, and distances from the second target anode to the center and from the second target cathode to the center are equal.

In Example 22, the subject matter of Example 21 may optionally be configured such that the distances from the second target anode to the first target anode, from the first target anode to the center, from the center to the first target cathode, and from the first target cathode to the second target cathode are equal.

In Example 23, the subject matter of any one or any combination of Examples 16-22 may optionally be configured such that the target multipole, which directionally and progressively stacks fractionalizations of target poles, includes a center, a first target anode separated from the center, and a second target anode separated from the first target anode. The second target anode may be further away from the center than the first target anode and the second target anode may have a higher fractionalization percentage then the first target anode. The target multipole may further include a first target cathode separated from the center, and a second target cathode separated from the first target cathode. The second target cathode may be further away from the center than the first target cathode and the second target cathode may have a higher fractionalization percentage then the first target cathode.

In Example 24, the subject matter of Example 16 may optionally be configured such that the target multipole, which directionally and progressively stacks fractionalizations of target poles, may include a third target anode on the anodic side of the center of the target multipole and a third target cathode on the cathodic side of the center of the target multipole.

In Example 25, the subject matter of any one or any combination of Examples 23-24 may optionally be configured such that the target multipole may further comprise a flanking target anode separated from the second target anode by the length, and a flanking target cathode separated from the second target cathode by the length.

In Example 26, the subject matter of any one or any combination of Examples 23-25 may optionally be configured such that the target multipole may further comprise flanking electrodes on opposing sides of the first target anode and having opposite polarity to the first target anode, flanking electrodes on opposing sides of the second target anode and having opposite polarity to the second target anode, flanking electrodes on opposing side of the first target cathode and having opposite polarity to the first target cathode, and flanking electrodes on opposing sides of the second target cathode and having opposite polarity to the second target cathode.

In Example 27, the subject matter of any one or any combination of Examples 16-26 may optionally be configured such that the method may further comprise receiving a user input to adjust an angle of an axis of linear progression for the target multipole.

In Example 28, the subject matter of any one or any combination of Examples 16-27 may optionally be configured such that the method may further comprise receiving a user input to adjust a focus of the target multipole to change a length of the linear electric field.

In Example 29, the subject matter of any one or any combination of Examples 16-28 may optionally be configured such that the method may further comprise receiving a user input to adjust a spread of the target multipole to change a width of the linear electric field.

In Example 30, the subject matter of any one or any combination of Examples 16-29 may optionally be configured such that the method may further comprise receiving as a user input a user-drawn region on an anatomical representation, automatically determining the target multipole based on the user input, the target multipole being used to determine the electrode fractionalizations for the plurality of electrodes.

In Example 31, the subject matter of any one or any combination of Examples 16-30 may optionally be configured such that the method may further comprise receiving as a user input a user-identified patient pain area, automatically determining the target multipole based on the user input, the target multipole being used to determine the electrode fractionalizations for the plurality of electrodes.

In Example 32, the subject matter of any one or any combination of Examples 16-31 may optionally be configured such that the method may further comprises displaying a gradient control element on a user interface, receiving a user input to adjust the gradient control element that is displayed on the user interface, and adjusting a strength of a therapy based on the adjusted gradient control element.

In Example 33, the subject matter of any one or any combination of Examples 16-32 may optionally be configured such that the method may further comprise automatically moving the target multipole within an array of electrodes.

In Example 34, the subject matter of any one or any combination of Examples 16-33 may optionally be configured such that the method may further comprise implementing a search heuristic to optimize a distance and amplitude on each pole in the target multipole to maximize an absolute value of the electric field.

In Example 35, the subject matter of any one or any combination of Examples 16-34 may optionally be configured such that the method may further comprise implementing the search heuristic to optimize for a number of poles in the target multipole, orientation angle of the electric field, focus of the electric field, and spread of the electric field.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, some features of the neuromodulation leads and a waveform generator.

FIG. 8 is a schematic view of a single electrical modulation lead implanted over approximately the longitudinal midline of the patient's spinal cord.

FIG. 9 illustrates an embodiment where an electrical modulation lead has been implanted more laterally with respect to the spinal cord, thereby placing it proximate the dorsal horn of the spinal cord, and the other electrical modulation lead has been implanted more medially with respect to the spinal cord, thereby placing it proximate the dorsal column of the spinal cord.

FIG. 20 illustrates an m×n transfer matrix used to determine the relative strengths of constituent current sources.

FIG. 27 illustrates, by way of example, a paddle lead, where a central point of stimulation (e.g. A) is identified, and a linear field may be centered around the central point of stimulation.

FIG. 28 illustrates, by way of example and not limitation, advanced controls that may be implemented within a base field design interface.

FIGS. 36A-38H illustrate, by way of example and not limitation, some addition examples of target multipoles that progressively stack fractionalization of target poles in a directional, progressive manner to produce a linear field.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
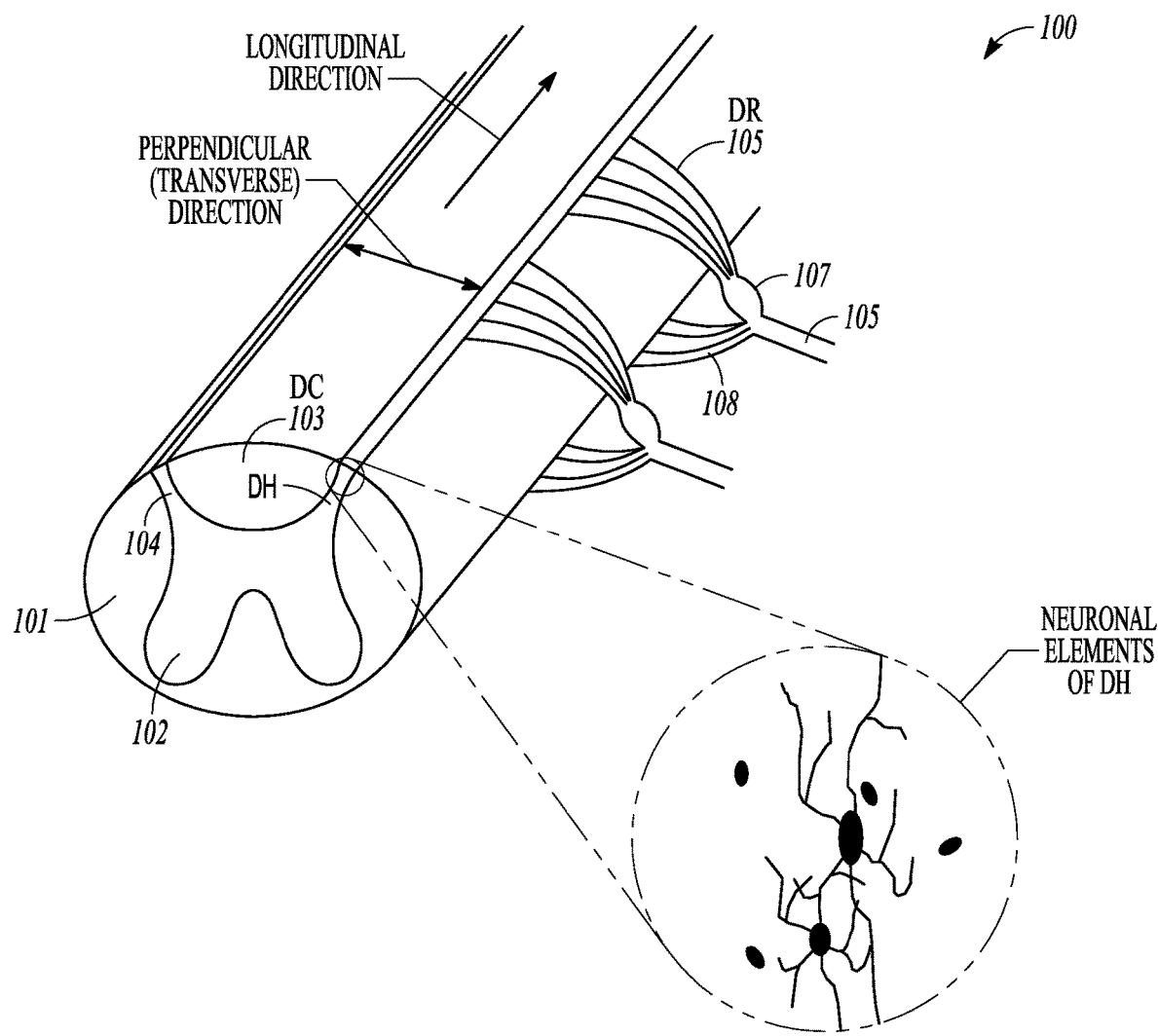
FIG. 1 illustrates, by way of example, a portion of a spinal cord.

Various embodiments described herein involve spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been conventionally targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1000 Hz or above) of the spinal cord that effectively blocks the transmission of pain signals in the afferent fibers in the DC. Some embodiments may implement this higher frequency modulation may include 1200 Hz or above, and some embodiments may implement this higher frequency modulation may include 1500 Hz or above. Some embodiments herein selectively modulate DH tissue, such as the presynaptic terminals of pain inhibitory neurons in the spinal cord, over DC tissue. Some embodiments selectively stimulate DR tissue and/or dorsal root ganglion over DC tissue to provide sub-perception therapy. As will be described in further detail below, some embodiments described herein target axons from inhibitory interneurons that propagate in anterior-posterior direction aligned with an electric field. Certain myelinated presynaptic terminals of inhibitory neurons oriented in the anterior-posterior (AP) direction, i.e. in parallel with electric field, may polarize more than their unmyelinated, differently oriented counterparts. Polarization may produce both subthreshold and suprathreshold effects that result in positive clinical effects, and sub-threshold progressive effects may also explain clinical observations of wash-in and wash-out effects. The terminal appears to may be the point of the greatest polarization. The unmyelinated dendrites to not polarize as much.

Such selective modulation is not delivered at these higher frequencies. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle. The selected modulation may be delivered with fixed widths. Although the target filed can be applied any pulse width that the device is capable of delivering, longer pulses widths are believed to be more effective.

Figure 2:
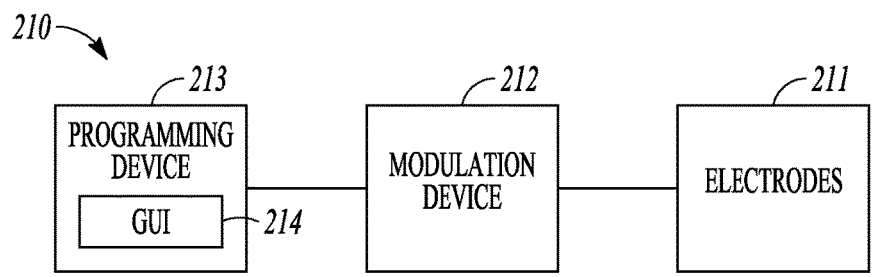
FIG. 2 illustrates, by way of example, an embodiment of a neuromodulation system.

FIG. 2 illustrates, by way of example, an embodiment of a neuromodulation system. The illustrated system 210 includes electrodes 211, a modulation device 212, and a programming system such as a programming device 213. The programming system may include multiple devices. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters. The modulation parameters may specify the electrical waveform (e.g. pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
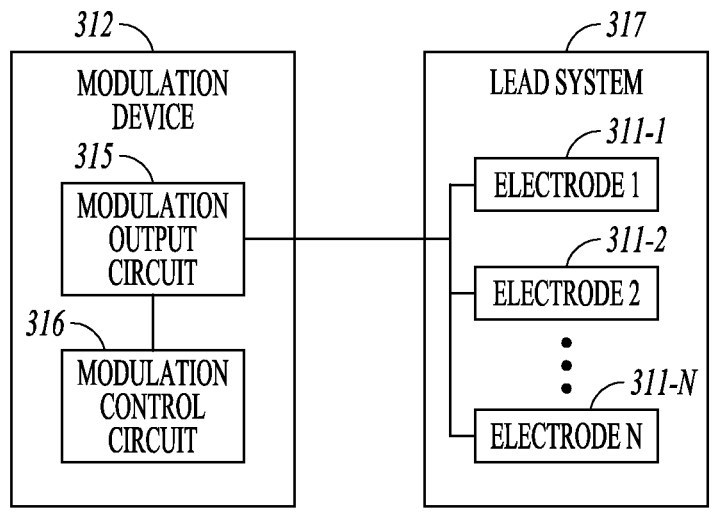
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers the neuromodulation. Neuromodulation pulses are provided herein as an example. However, the present subject matter is not limited to pulses, but may include other electrical waveforms (e.g. waveforms with different waveform shapes, and waveforms with various pulse patterns). The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes a paddle lead.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g. pulses), presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Figure 4:
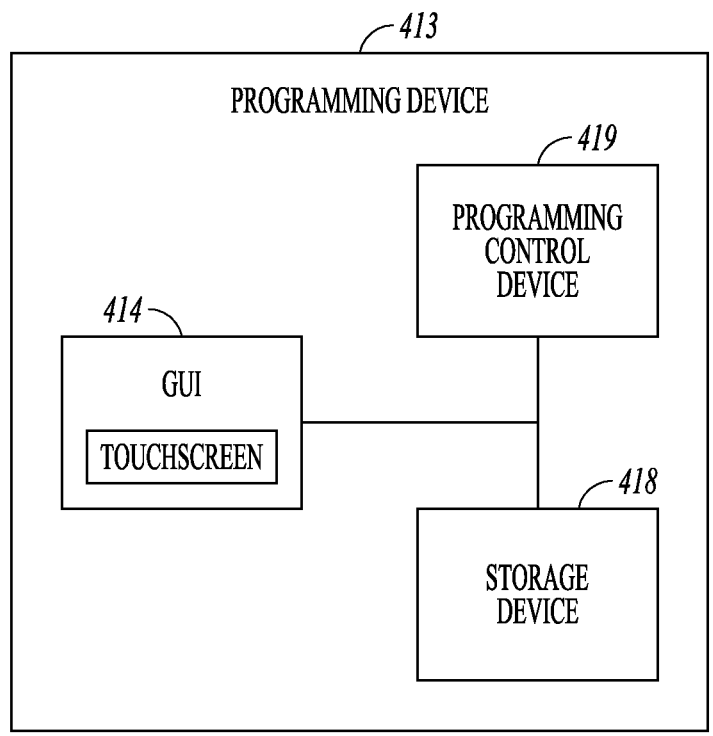
FIG. 4 illustrates, by way of example, an embodiment of a programming system such as a programming device, which may be implemented as the programming device in the neuromodulation system of FIG. 2.

FIG. 4 illustrates an embodiment of a programming system such as a programming device 413, which may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
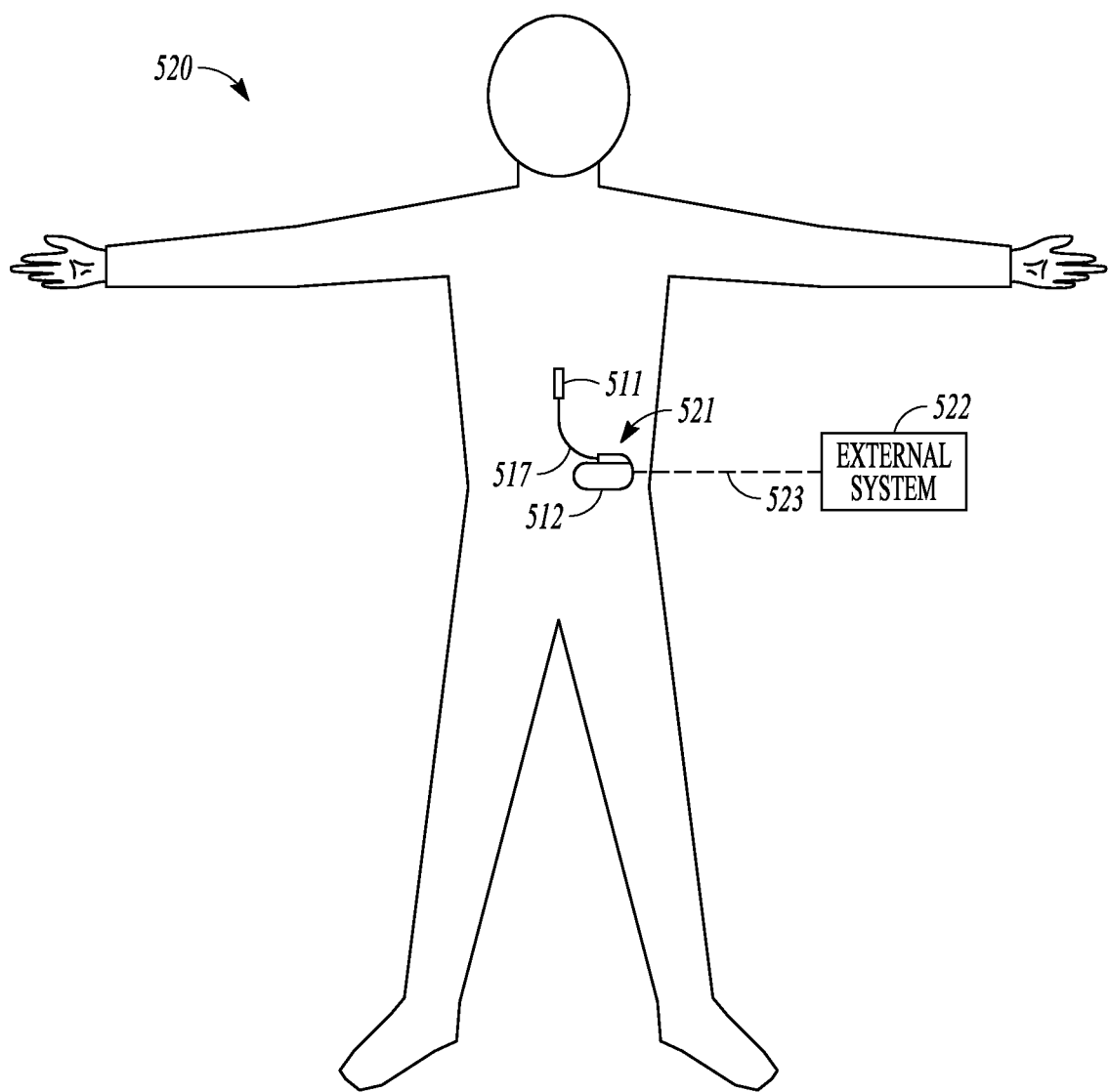
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 522 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
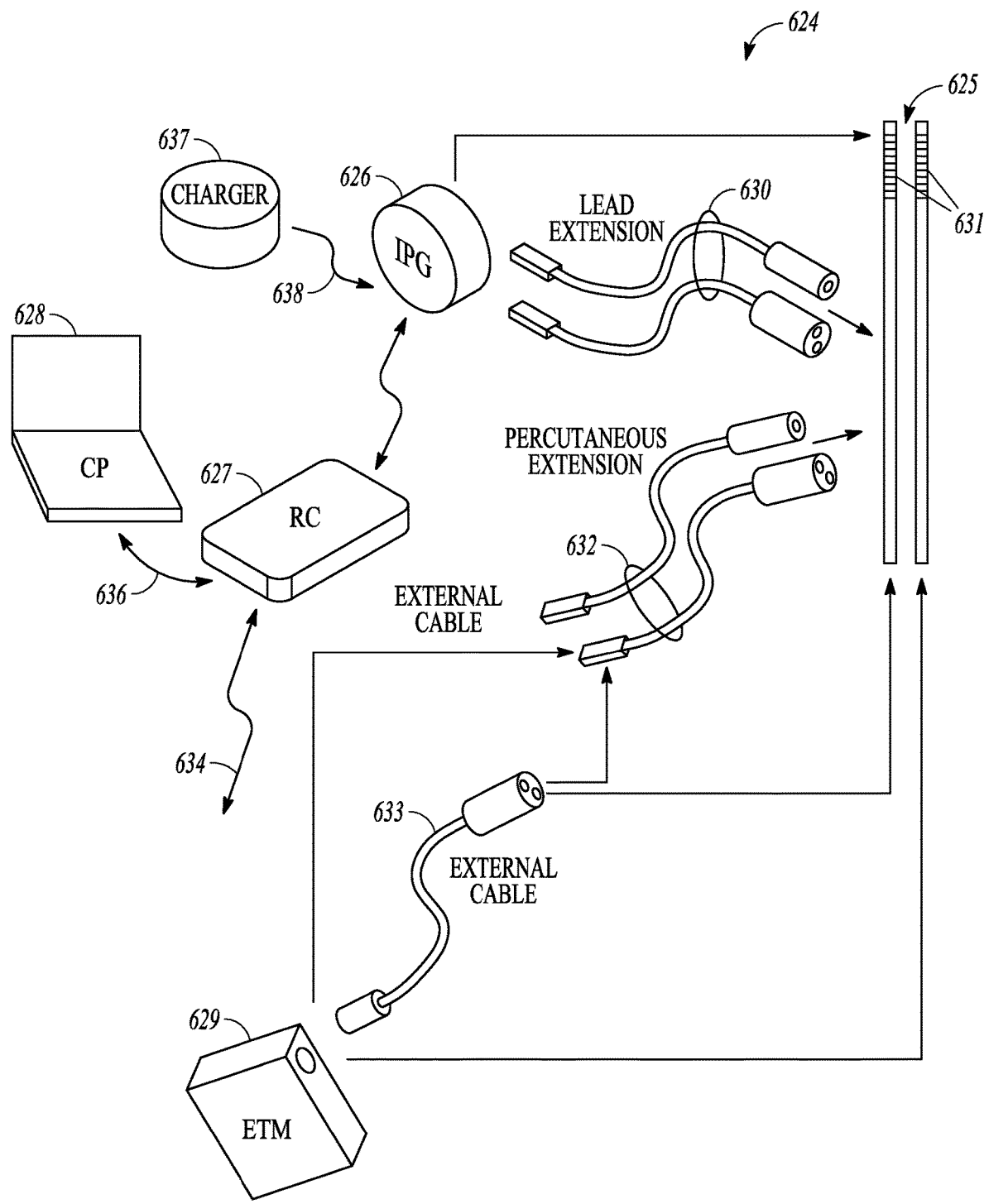
FIG. 6 illustrates, by way of example, an embodiment of a SCS system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an electrical waveform generator 626, an external remote controller RC 627, a clinician's programmer (CP) 628, and an external trial modulator (ETM) 629. IPGs are used herein as an example of the electrical waveform generator. However, it is expressly noted that the waveform generator may be configured to deliver repeating patterns of pulses, irregular patterns of pulses where pulses have differing amplitudes, pulse widths, pulse intervals, and bursts with differing number of pulses. It is also expressly noted that the waveform generator may be configured to deliver electrical waveforms other than pulses. The waveform generator 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the waveform generator case function as a case electrode) to allow for lateral steering of the current. Alternatively, a surgical paddle lead can be used in place of one or more of the percutaneous leads. In some embodiments, the waveform generator 626 may include pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar waveform generation circuitry as the waveform generator 626 to deliver electrical modulation energy to the electrodes accordance with a set of modulation parameters. The ETM 629 is a non-implantable device that is used on a trial basis after the neuromodulation leads 625 have been implanted and prior to implantation of the waveform generator 626, to test the responsiveness of the modulation that is to be provided. Functions described herein with respect to the waveform generator 626 can likewise be performed with respect to the ETM 629.

The RC 627 may be used to telemetrically control the ETM 629 via a bi-directional RF communications link 634. The RC 627 may be used to telemetrically control the waveform generator 626 via a bi-directional RF communications link 635. Such control allows the waveform generator 626 to be turned on or off and to be programmed with different modulation parameter sets. The waveform generator 626 may also be operated to modify the programmed modulation parameters to actively control the characteristics of the electrical modulation energy output by the waveform generator 626. A clinician may use the CP 628 to program modulation parameters into the waveform generator 626 and ETM 629 in the operating room and in follow-up sessions.

The CP 628 may indirectly communicate with the waveform generator 626 or ETM 629, through the RC 627, via an IR communications link 636 or other link. The CP 628 may directly communicate with the waveform generator 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the waveform generator 626 to allow the desired parameters to be determined based on patient feedback or other feedback and for subsequently programming the waveform generator 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant waveform generator, implant waveform generator and lead(s), replace waveform generator, replace waveform generator and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the waveform generator via a wireless link such as an inductive link 638. Once the waveform generator has been programmed, and its power source has been charged by the external charger or otherwise replenished, the waveform generator may function as programmed without the RC or CP being present.

FIG. 7 illustrates, by way of example, some features of the neuromodulation leads 725 and a waveform generator 726. The waveform generator 726 may be an implantable device or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable waveform generator may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The waveform generator may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the waveform generator. Electrical modulation energy is provided to the electrodes in accordance with a set of modulation parameters programmed into the pulse generator. By way of example but not limitation, the electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the case of the waveform generator. The system may be capable of transmitting modulation energy to the tissue in a monopolar or multipolar (e.g., bipolar, tripolar, etc.) fashion. Monopolar modulation occurs when a selected one of the lead electrodes is activated along with the case of the waveform generator, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The waveform generator may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The waveform generator may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

FIGS. 8-11 illustrate, by way of example, a difference in electrical field strength in the longitudinal and transverse directions when the current is fractionalized such that the electrical field in the longitudinal direction generated by the fractionalized current delivered to each electrode is approximately equal. The voltage at a patient's spinal cord (especially at the DC fibers) is approximately equal in the longitudinal direction, resulting in a voltage gradient of approximately zero along the DC. This may require different amounts of fractionalized current delivered to each electrode. Calibration techniques are used to determine the proper current fractionalization. With the current fractionalized to a plurality of electrodes on the electrical modulation lead, the resulting field can be calculated by superimposing the fields generated by the current delivered to each electrode. Moreover each electrical field has a longitudinal component and a transverse component.

FIG. 8 is a schematic view of a single electrical modulation lead 839 implanted over approximately the longitudinal midline of the patient's spinal cord 840. It is understood that additional leads or lead paddle(s) may be used, such as may be used to provide a wider electrode arrangement and/or to provide the electrodes closer to dorsal horn elements, and that these electrode arrays also may implement fractionalized current. FIG. 9 illustrates an embodiment where an electrical modulation lead 941 has been implanted more laterally with respect to the spinal cord, thereby placing it proximate the dorsal horn of the spinal cord, and the other electrical modulation lead 942 has been implanted more medially with respect to the spinal cord, thereby placing it proximate the dorsal column of the spinal cord 940. Placement of the lead more proximate to the DH than the DC may be desirable to preferentially stimulate DH elements over DC neural elements for a sub-perception therapy. Any other plurality of leads or a multiple column paddle lead can also be used. Longitudinal component of the electrical field is directed along the y-axis depicted in FIG. 8, and a transverse component of the electrical field is directed along the x-axis depicted in FIG. 8. Some embodiments may include directional leads with one or more directional electrodes. A directional electrode may extend less than 360 degrees about the circumference of a lead body. For example, a row of two or more directional electrodes (e.g. "segmented electrodes") may be positioned along the circumference of the lead body. Activating select ones of the segmented electrodes may help extend and shape the field in a preferred direction.

Figure 10:
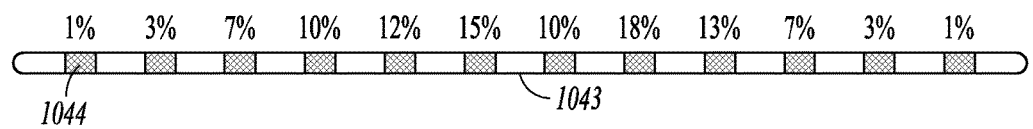
FIG. 10 is a schematic view of the electrical modulation lead showing an example of the fractionalization of the anodic current delivered to the electrodes on the electrical modulation lead.

FIG. 10 is a schematic view of the electrical modulation lead 1043 showing an example of the fractionalization of the anodic current delivered to the electrodes on the electrical modulation lead. In order to provide a simpler illustration, these figures illustrate fractionalization using monopolar modulation where a case electrode of the waveform generator is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 10, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various embodiments described herein implement a programmed algorithm to determine the appropriate fractionalization to achieve a desired modulation field property (e.g. constant electric field, or constant electric field magnitude, or constant voltage).

Figure 11:
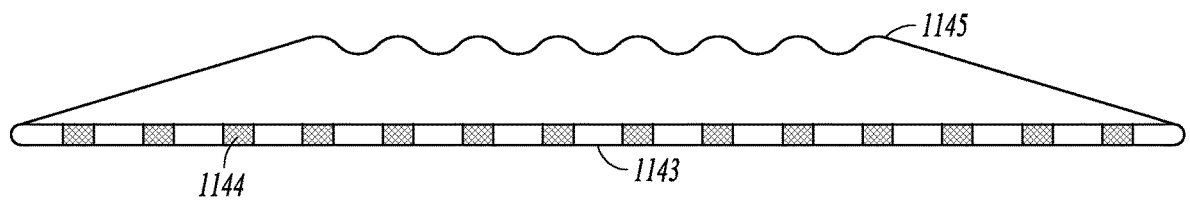
FIG. 11 illustrates, by way of example, a schematic illustration of a gradient in the longitudinal direction along the axis of the electrical modulation lead.

FIG. 11 illustrates, by way of example, a schematic illustration of a gradient in the longitudinal direction along the axis of the electrical modulation lead. The electrical field strength 1145 in the longitudinal direction is plotted over a schematic representation of the electrodes 1144 on the electrical modulation lead 1143. The illustration in FIG. 11 shows that the electrical field strength is substantially constant over the middle portion of the electrical modulation lead, but may form a wave with very small amplitude because of the gaps between the electrodes in the lead. This substantially constant electrical field forms a small longitudinal gradient, which minimizes activation of the large myelinated axons in the dorsal column. The illustration in FIG. 11 also shows the electrical field in the longitudinal direction tapering at the ends of the electrical modulation lead.

Figure 12:
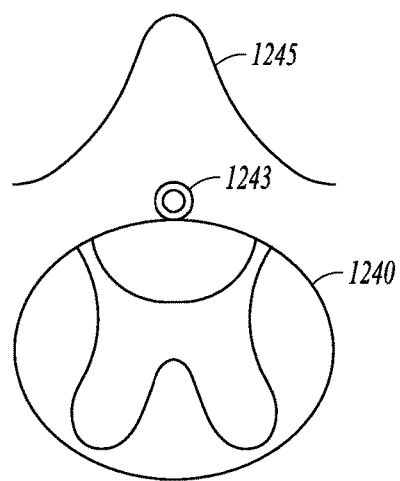
FIG. 12 illustrates, by way of example, a schematic illustration of a gradient in the transverse direction.

FIG. 12 illustrates, by way of example, a schematic illustration of a gradient in the transverse direction. The transverse electrical field strength 1245 in the transverse direction is plotted over a schematic representation of the electrical modulation lead 1243 and the spinal cord 1240 of the patient. The illustration in FIG. 12 shows that the transverse electrical field strength is greatest adjacent the electrical modulation lead and falls off lateral of the electrical modulation lead. Use of additional modulation leads to widen the electrode array may be used to provide desired fractionalization to also provide a region of a substantially constant electric field for a distance along the transverse direction. Substantially constant electric fields favor modulation of dorsal horn and/or dorsal root neuronal elements over dorsal column neuronal elements. Various embodiments use a substantially constant electric field to target inhibitory interneurons that propagate in anterior-posterior direction.

Figure 13:
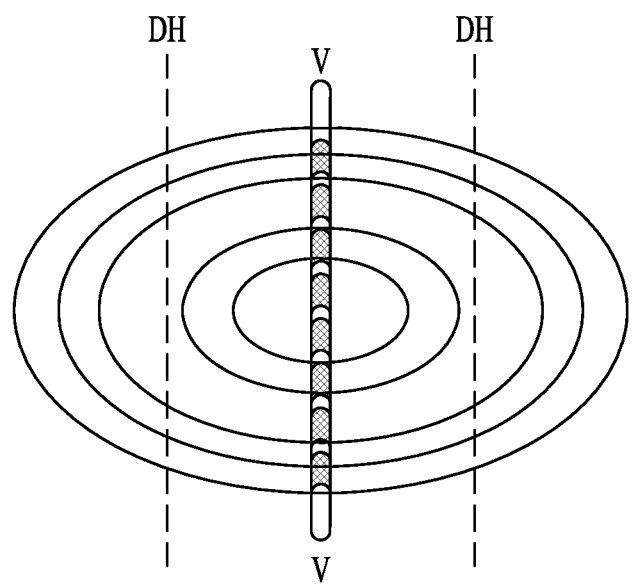
FIG. 13 illustrates, by way of example, equipotential voltage lines for a lead, along with a representation of the lead and the dorsal horns.
Figure 14:
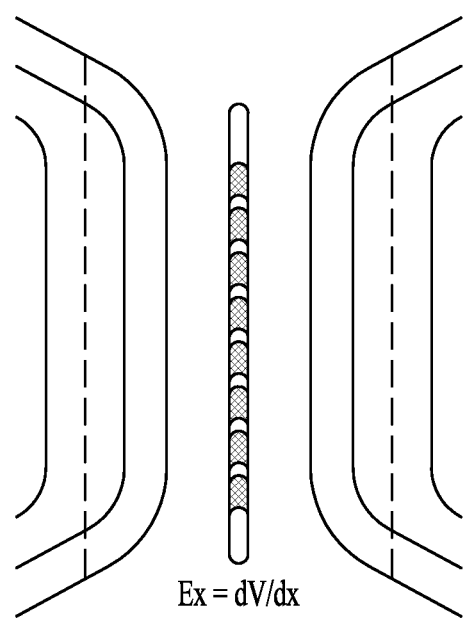
FIGS. 14-15 illustrate, by way of example, a substantial uniform electric field, along with a representation of the lead and the dorsal horns.
Figure 15:
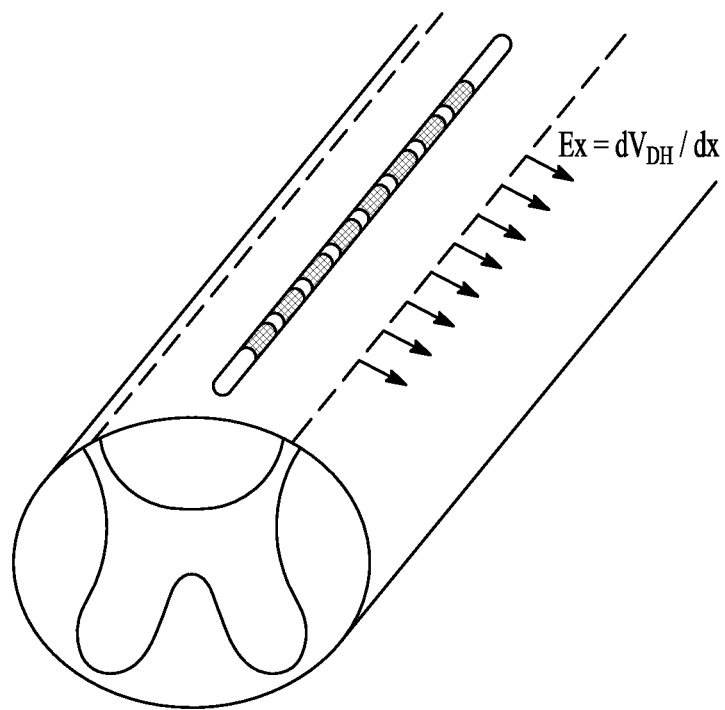

FIG. 13 illustrates, by way of example, equipotential voltage lines for a lead, along with a representation of the lead and the dorsal horns; and FIGS. 14-15 illustrate, by way of example, a substantial uniform electric field, along with a representation of the lead and the dorsal horns. The orientation of the electrical field may be selected to target the different directions/orientations of the DH elements. To generate electrical fields in different medio-lateral directions, the electrodes may have different current fractionalizations in the radial direction. FIG. 15 illustrates Ex as a field in the X direction. It is noted that the target multipoles discussed herein may be used to create a linear field other directions such as a field (Ey) in the Y direction.

The SCS system may be configured to deliver different electrical fields to achieve a temporal summation of modulation in the DH elements. For embodiments that use a pulse generator, the electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

An embodiment modifies the fractionalized current delivered to each electrode to minimize the electrical field gradient in the longitudinal direction, so as to minimize activation of the DC elements. Minimizing activation of the DC elements can include a model-based calculation, where the model includes the information from the calibration. A discrete activating function can be calculated by the formula: $AF(n)=Ga/(\pi \times d \times 1) \times [Ve(n-1)-2\ Ve(n)+Ve(n+1)]$, wherein Ga is the axonal intermodal conductance, d is the axonal diameter, 1 is the length of the node of Ranvier, Ve(n) is the strength of the electric field at the node for which the activating function is determined, Ve(n-1) is the strength of the electric field at the node preceding the node for which the activating function is determined, and Ve(n+1) is the strength of the electric field at the node following the node for which the activating function is determined. Using this formula, the discrete activating function is calculated from the conductance normalized to the surface area of the node of Ranvier.

Modulation thresholds vary from patient to patient and from electrode to electrode within a patient. An electrode/tissue coupling calibration of the electrodes may be performed to account for these different modulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the modulation signal strength of the electrical pulse train delivered when the control element is actuated. Other sensed parameter or patient-perceived modulation values (e.g. constant paresthesia, or maximum tolerable paresthesia) may be used to provide the electrode/tissue coupling calibration of the electrodes. These sensed parameter or patient-perceived modulation values may be used to estimate the current fractionalization by minimizing the sum of the square of the discrete activating function divided by the determined value (e.g. perception threshold) at each electrode on an electrical modulation lead as is described in more detail below. Squaring the discrete activating function, or any driving force from the electrical field, eliminates the differences in depolarizing and hyperpolarizing fields. The current fractionalization that results in a minimize sum minimizes the field gradient in the longitudinal direction.

Various embodiments of the present subject matter may use "target multipoles" to provide a linear field that may maximize the electric field in a region while minimizing the activation of dorsal columns. These target multipoles may be referred to as "ideal" or "virtual" multipoles. Each target pole of a target multipole may correspond to one physical electrode, but may also correspond to a space that does not correspond to one electrode, and may be emulated using electrode fractionalization. By way of examples, U.S. Pat. Nos. 8,412,345 and 8,909,350 describe target multipoles. U.S. Pat. Nos. 8,412,345 and 8,909,350 are hereby incorporated by reference in their entirety. Target multipoles are briefly described herein.

A stimulation target in the form of a target poles (e.g., a target multipole such as a target bipole or target tripole or a target multipole with more than three target poles) may be defined and the stimulation parameters, including the fractionalized current values on each of the electrodes, may be computationally determined in a manner that emulates these target poles. Current steering may be implemented by moving the target poles about the leads, such that the appropriate fractionalized current values for the electrodes are computed for each of the various positions of the target pole.

Figure 16A:
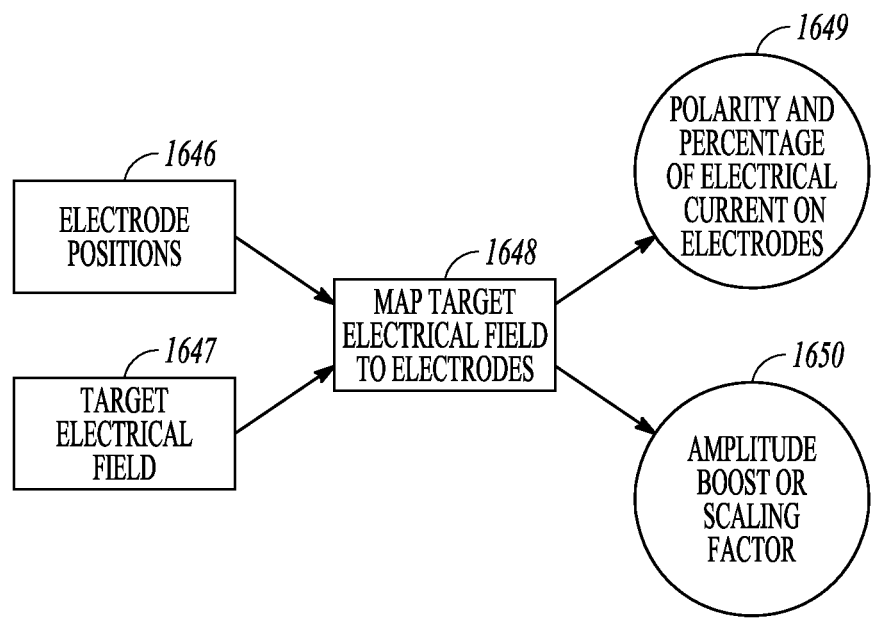
FIG. 16A illustrates, by way of example, mapping of target electrical fields to electrodes.

With reference to FIG. 16A, the CP may be configured to accept relative electrode positions 1646 and a representation of an target electrical field 1647 (instead of including these parameters in the design of navigation tables) and maps the target electrical field to the electrodes 1648, thereby yielding the polarities and percentages of electrical current to be associated with the electrodes 1649, as well as a boost or scaling factor 1650 for globally adjusting the magnitude of the total current supplied to the electrodes to maintain a perceived intensity level of the electrical stimulation. Electrode locations and information about the desired electrical field may be independently inputted into the algorithm.

Figure 16B:
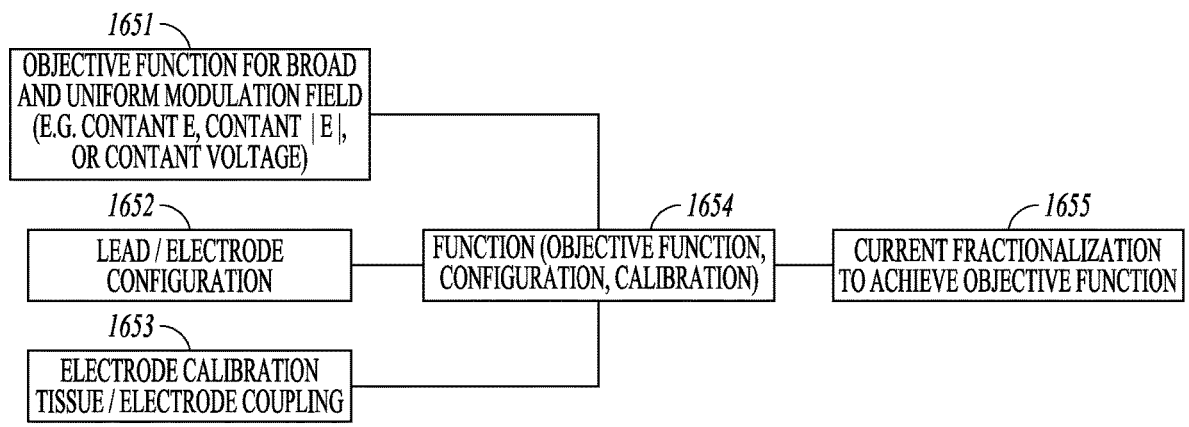
FIG. 16B illustrates, by way of example, an embodiment for determining fractionalization to achieve an objective function.

FIG. 16B illustrates, by way of example, an embodiment for determining fractionalization to achieve an objective function. An objective function refers to a function with desirable characteristics for modulating the targeted tissue. The objective function may also be referred to as an objective target function. An objective function 1651 for a broad and uniform modulation field is identified for a given volume of tissue. Examples of an objective function includes a constant E (electric field), a constant |E| (electric field magnitude), and a constant voltage. The lead and electrode configuration 1652 are also identified, as well as calibration for electrode tissue coupling 1653. A function 1654 is performed that is dependent on the objective function, the lead and electrode configuration and the calibration. The result of the function is the fractionalization of modulation energy (e.g. current) 1655 for each electrode to achieve the objective function.

Figure 17:
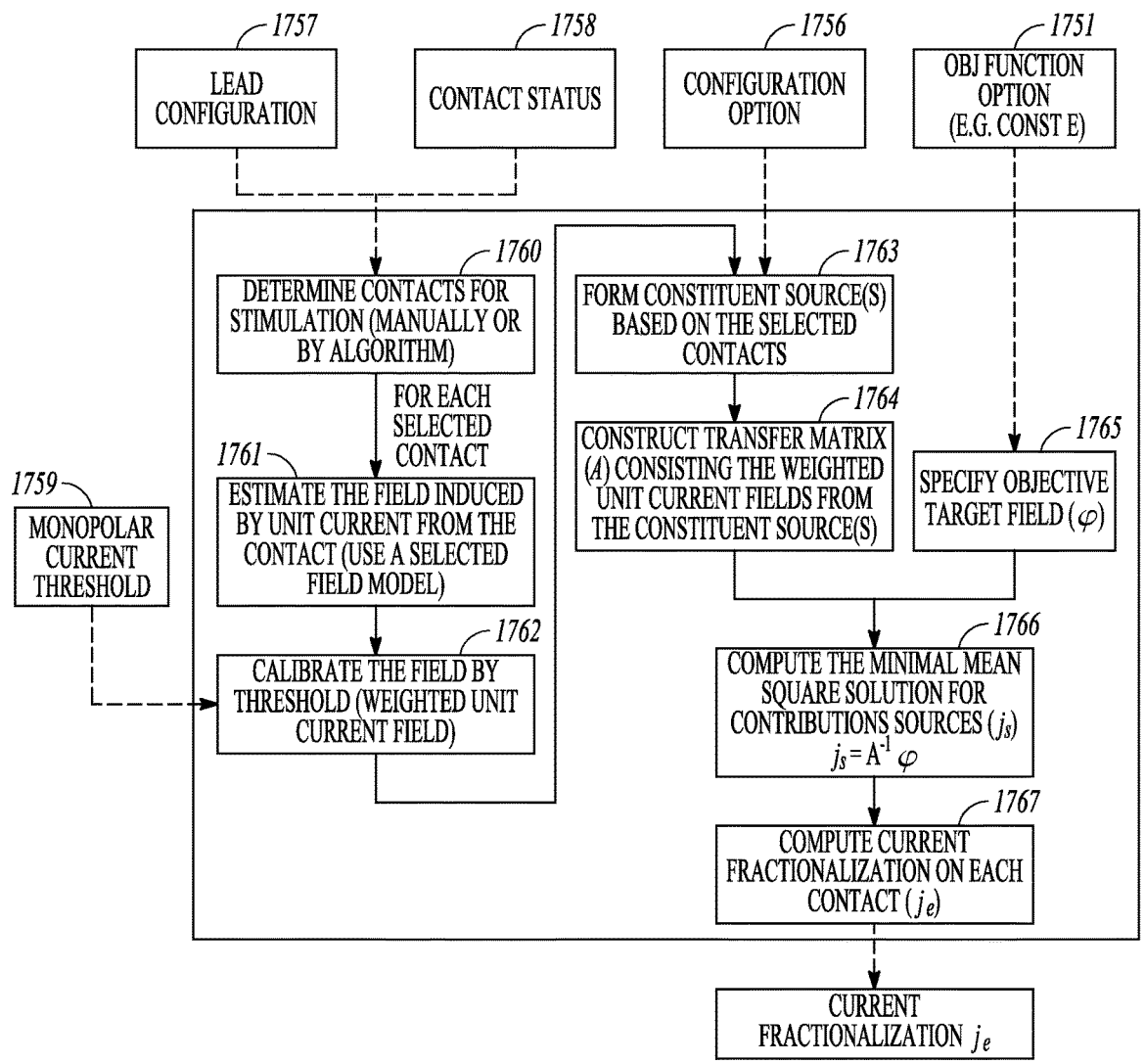
FIG. 17 illustrates, by way of example, an embodiment for determining fractionalization to achieve an objective function with more detail.

FIG. 17 illustrates, by way of example, an embodiment for determining fractionalization to achieve an objective function with more detail. An objective target function 1751 (e.g. constant E) is provided as an input to a process. Other inputs to the process include a configuration option 1756, a lead configuration 1757 and electrode contact status 1758, and a threshold 1759 such as a current threshold or more particularly a monopolar current threshold. The lead configuration 1757 and contact status 1758 identify an electrode arrangement, identifying a position of each electrode to determine the field. The overall field is a superimposed field from each electrode. The configuration option 1756 refers to monopolar (same polarity for all activated electrodes) and multipolar options (combined anode and cathodes in field). The threshold is used to compensate for electrode/tissue coupling differences.

The contacts for stimulation may be determined automatically or manually 1760 from the lead configuration and contact status. A selected field model may be used to estimate the field induced by unit current from the contact 1761. The field is calibrated using the threshold 1762. For example, the unit current field may be weighted. Constituent forces are formed based on the selected contacts 1763, and a transfer matrix 1764 is constructed to use to compute the minimal mean square solution 1766 using contributions from the constituent sources and using a specified target field 1765. The solution can be used to compute the current fractionalization on each contact 1767.

Figures 18A, 18B:
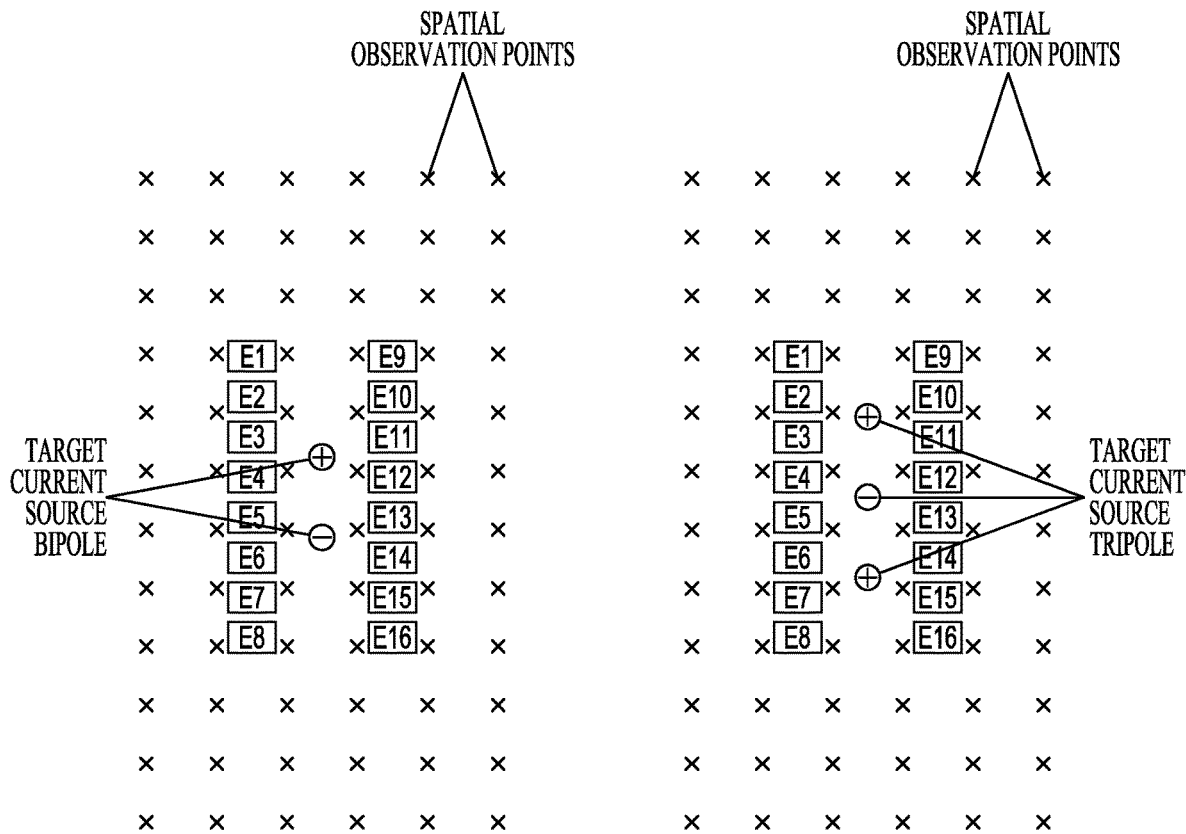
FIGS. 18A-18B illustrate, by way of example, mapping a target electrical field to an electrode array.

With reference to FIGS. 18A-18B, the CP may map a target electrical field to the electrode array by estimating the field potential values (or some other linear electrical parameter, such as an activating function, current density, etc.) of the target field at a plurality of spatial observation points. The CP may accomplish this by determining the desired locations of target current source poles relative to the electrode array, and modeling an electrical field generated by the target current source poles to determine desired field potential values at the spatial observation points (e.g., using analytical and/or numerical models).

Figures 19A, 19B, 19C:
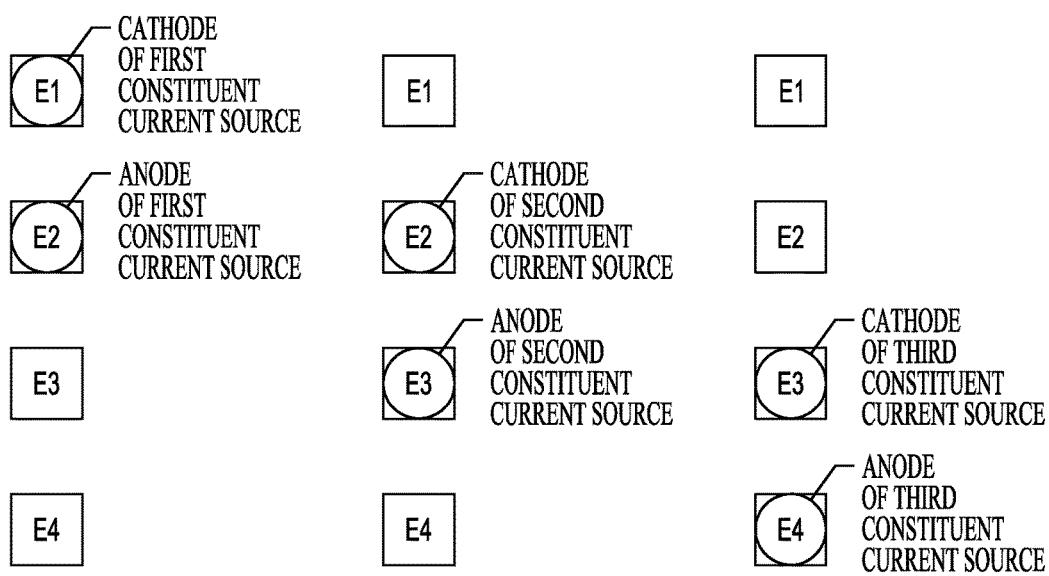
FIGS. 19A-19C, illustrate, by way of example, selection of a plurality of constituent current sources at the locations of the electrodes.

Although target current source poles are one way to represent a "target electrical field", other representations of target fields may be used. The locations of the target current source poles may be determined in a manner that places the resulting electrical field over an identified region of the patient to be stimulated. The spatial observation points may be spaced in a manner that would, at the least, cover the entire tissue region to be stimulated and/or a tissue region that should not be stimulated. The locations of the target current source poles may be defined by the user, and may be displayed to the user along with the electrode locations, which as briefly discussed above, may be determined based on electrical measurements taken at the electrodes. Referring to FIGS. 19A-19C, the CP may select, or allow a user to select, a plurality of constituent current sources at the locations of the electrodes. The locations of the electrodes may be determined based on measurements taken at the electrodes in response to sub-threshold electrical signals transmitted between the electrodes. In the illustrated target bipole a first constituent current source can be defined at the locations of electrodes E1 and E2 as −100% and +100%, respectively (FIG. 19A); a second constituent current source can be defined at the locations of electrodes E2 and E3 as −100% and +100%, respectively (FIG. 19B); a third constituent current source can be defined at the locations of electrodes E3 and E4 as −100% and +100%, respectively (FIG. 19C); and so on. The location of each of the electrodes is included within at least one of the constituent sources. Thus, the minimum number of constituent sources may be equal to the number of contacts less one, or may equal the number of contacts (e. g., if a monopole is used as the constituent source).

Once the constituent sources are selected, the CP may determine the relative strengths of the constituent current sources that, when combined, result in estimated electrical field potential values at the spatial observation points that best matches the desired field potential values at the spatial observation points. In particular, the CP may model the constituent current sources (e.g., using analytical and/or numerical models) and estimate the field potential values per unit current (V/mA) generated by each of the constituent current sources at the spatial observation points, and may generate an m×n transfer matrix (shown in FIG. 20) from the estimated field potential values per unit current, with m equaling the number of spatial observation points and n equaling the number of constituent sources. The relative strengths of the constituent current sources may be determined using an optimization function that includes the transfer matrix A and the desired field potential values.

The optimization function may be a least-squares (overdetermined) function expressed as: $|\varphi - A\hat{j}|^2$, where $\varphi$ is an m-element vector of the desired field potential values, A is the transfer matrix, and $\hat{j}$ is an n-element vector of the strengths of the constituent current sources. The constituent current source strengths $\hat{j}$ may be solved such that the optimization function $|\varphi - A\hat{j}|^2$ is minimized. The square difference is minimized if $\varphi = A\hat{j}$. One approach for solving this problem may be to invert the transfer matrix A and pre-multiply, such that $A^{-1} = \gamma A^{-1} A\hat{j}$, which yields the solution $\hat{j} = A^{-1}\varphi$. Once the strengths of the constituent current sources are determined, the CP converts these strengths to current distributions on the electrodes in the form of a polarity and percentage.

The remainder of this document discusses various embodiments that relate to enhancing the effectiveness a modulation field such as a sub-perception modulation field, various embodiments that relate to the electrode selection and refinement for use in delivering a modulation field such as a sub-perception field. These embodiments may be implemented separately, or may be implemented in various combination(s). Such combination(s) may be useful for delivering sub-perception modulation of the DH or DR tissue over DC tissue. However, some embodiments may be used to deliver other modulation therapies.

Neural tissue in the region of the spinal cord has different characteristics. For example, DC fibers (mostly myelinated axons) run in an axial direction, whereas DH (e.g. neuronal cell terminals, neuronal cell bodies, dendrites, and axons) fibers are oriented in many directions. The distance from typically-placed epidural SCS leads to DH fibers are different than the distance from these leads to DC fibers. Further, DH fibers and dorsal column fibers have different responses (e.g. activation functions) to electrical modulation. The strength of modulation (i.e., depolarizing or hyperpolarizing) of the DC fibers and neurons is described by the so-called "activation function" which is proportional to the second-order spatial derivative of the voltage along the longitudinal axis of the spine ($\partial 2V/\partial x2$). This is partially because the large myelinated axons in DC are primarily aligned longitudinally along the spine. On the other hand, the likelihood of generating action potentials in DH fibers and neurons is described by an activating function that is proportion to the first-order spatial derivative of the voltage along the spine ($\partial V/\partial x$), which is otherwise known as the electric field. Thus, the DH activating function is proportional to the first-order derivative of the voltage along the fiber axis, whereas the DC activating function is proportional to the second-order derivative of the voltage along the fiber axis. Accordingly, the distance from the electrical field locus affects the DH activating function ($\partial V/\partial x$) less than it affects the dorsal column activating function $\partial 2V/\partial x2$. The neuronal elements (e.g., neurons, dendrites, axons, cell bodies, and neuronal cell terminals) in the DH can be preferentially stimulated over the DC neuronal elements by minimizing the longitudinal gradient of an electrical field generated by a neuromodulation lead along the DC, thereby providing therapy in the form of pain relief without creating the sensation of paresthesia. This technique relies, at least partially on the natural phenomenon that DH fibers and DC fibers have different responses (activation functions) to electrical modulation.

Various embodiments for enhancing modulation field selectively modulate DH and/or DR tissue over DC tissue. Conventional SCS activates DC fiber axons, and the orthodromic propagation of action potentials induces perception of paresthesia in the brain and antidromic propagation of action potentials to fiber collaterals and terminals ending in DH evokes pain control mechanism in DH. Various embodiments shape the stimulation field to preferably stimulate fiber terminals ending in DH and/or DR to provide pain relief without inducing paresthesia. For example, uniformity in a first order gradient of voltage (i.e. uniformity in electric field) may be more efficient in stimulating DH fiber terminals and/or stimulating DR fibers. Uniformity across a larger field may eliminate the needs for searching optimal stimulation site and create broader coverage of pain. For example, the uniformity may extend between or among two or more electrodes within an arrangement of electrodes. In other examples, the uniformity may extend among three, four, five, six or more electrodes within an arrangement of electrodes to eliminate the needs for searching for an optimal simulation site and creating a broader therapeutic coverage. Thus, the uniformity extends over a substantial portion of the lead. Some embodiments are configured to determine a modulation parameter set to create a field shape to provide a broad and uniform modulation field to enhance modulation of targeted neural tissue (e.g. DH tissue or DR tissue). Some embodiments are configured to determine a modulation parameter set to create a field shape to reduce or minimize modulation of non-targeted tissue (e.g. DC tissue). Various embodiments disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of DH neural tissue and to minimize the modulation of DC tissue. A benefit of MICC is that MICC accounts for various in electrode-tissue coupling efficiency and perception threshold at each individual contact, so that "hot-spot" stimulation is eliminated.

The modulation field may be shaped to provide a constant electric field (E) at the DH tissue in a selected direction. The electric field (E) at the DH in any direction is the negative gradient (negative rate of change) of the scalar potential field (V) in that direction. Due to the linearity of field superposition, a transfer function can be formed to estimate the EDH(x,y,z) at selected direction induced by unit current from a single electrode located at (x0, y0, z0), the total E field is the linear combination of the E field induced by currents from each active electrode weighted by the current fractionalization. In an example, the modulation field may be a constant V field along the DC tissue.

Due to the linearity of field superposition, a transfer function can be formed to estimate the VDC(x,y,z) at selected direction induced by unit current from a single electrode located at (x0, y0, z0), the total V field is the linear combination of the V field induced by currents from each active electrode weighted by the current fractionalization.

Various embodiments predict the amplitude. For example, the target V magnitude at DC or the target E magnitude at DH may be determined as a percentage of perception threshold of current (Ith) under certain modulation configuration (monopole, bipole or tripole, etc). For example, a set of V magnitude at selected locations of DH can be estimated as Vtarget using mathematical model under the monopolar Ith (or under the desired percentage of Ith) from a selected electrode. When current is fractionalized among more than one electrode, the total amplitude can be estimated as the one that would maximally approximate the Vtarget from the combination of current fractionalization. An empirical method may estimate the Ith under the desired fractionalization and adjust the amplitude down.

Various embodiments provide a method for modulating a volume of tissue with an activation function, where the method includes selecting a modulation field to modulate the volume of tissue, including selecting an objective function for the modulation field that is specific to the volume of tissue and the activation function of the volume of tissue. The objective function for the modulation field promotes uniformity of a modulation response in the volume of tissue. The volume of tissue may be modulated using the selected modulation field with the selected objective function. The objective function may be an objective function to modulate DH tissue and/or DR tissue. Examples of such an objective function include a constant E objective function or a constant |E| objective function.

Conventional spinal cord stimulation at rates lower than 1.2 kHz use perceived paresthesia within the area of pain to cover the pain. No paresthesia with high rate paradigms—suggests activation of non-dorsal column elements. Also, pain relief appears to develop only after a latent period of some hours. The long therapeutic wash-in time suggests sub-threshold effects. These observations hint that it may be desirable to find stimulation targets other the dorsal column.

Axons from inhibitory interneurons propagate in anterior-posterior direction, aligned with bipole (i.e. E-field). The axon length is less than 3 length constants (length=1 mm) so voltages can propagate from cell body to tip. The axon is myelinated which increases the length constant, decreases the filtering effect of membrane, and results in activating function being first difference vs. derivative. The neuron is located at center of bipole where |E| is strongest. Certain myelinated and unmyelinated presynaptic terminals of inhibitory neurons are oriented in an anterior-posterior (AP) direction, i.e. in parallel with electric field may polarize more than their unmyelinated, differently oriented counterparts. Polarization may produce both subthreshold and suprathreshold effects that result in positive clinical effects, and sub-threshold progressive effects may also explain clinical observations of wash-in and wash-out effects. The terminal appears to be the point of greatest polarization, whereas the unmyelinated dendrites do not polarize as much.

Various embodiments of the present subject matter provide DH modulation with a constant or near constant electric field in the volume of DH tissue to enhance the modulation of DH tissue or nerve root tissue. DH tissue is described below as an example. Preferential engagement of DH tissue may facilitate pain relieve without the need for modulation-induced sensation. Electrodes may be selected and electrode polarities and strengths may be designed to be approximately constant in the superficial DH along the full electrode or the portion(s) of the array deemed important for therapy. Some embodiments may modulate DH in bursts of pulses to enhance the effectiveness of exciting axon terminals in the DH. Data in cat spinal cord ventral horn suggest that consecutive pulses close in time are particularly effective as exciting terminals, and showed this with a burst of 4 pulses that decreased the threshold by ~4× (intra-burst frequency of about 500 Hz; Gustaffson et al., 1976). Pulse delivery at continuous high rate (equal to or greater than a few hundred Hz) may also effectively excite the terminals, but a burst is expected to be efficient.

Furthermore, various embodiments of the present subject matter relate to a new field shape designed with the purpose of selectively activating presynaptic terminals of pain inhibitory neurons in the spinal cord, various embodiments of the present subject matter relate to an interface to control this field, and various embodiments of the present subject matter relate to mathematically-based search heuristics to optimize fields to activate specific neural elements. Electrode configurations and fractionalizations are used to create a target multipole configuration with a linear change in potentials between poles of the target multipole. The target multipole configuration may be manually configured, built into a device, or matched using existing forward/inverse modeling techniques. The interface provides a means to define the parameters of the field. Examples of parameters that may be defined may include parameters such as polar orientation, field slope, field width, and the like. The field may be optimized using mathematical search heuristics (either off line or in real time) to derive field shapes faithful to this concept according to desired activation targets, a mathematical "cost function", or some other outcome measure.

Although it has been known that first derivative of extracellular V activates terminals, a field has not been designed to maximize the linear progression of extracellular voltages in the Rostral-Caudal direction for subthreshold and suprathreshold activation of terminals oriented in the anterior posterior (AP) direction. Various embodiments of the present subject matter produce a linear field by stacking fractionalizations of target poles in a directional, progressive manner as generally discussed with respect to FIGS. 21A-21E by way of example and not limitation.

Figure 21A:
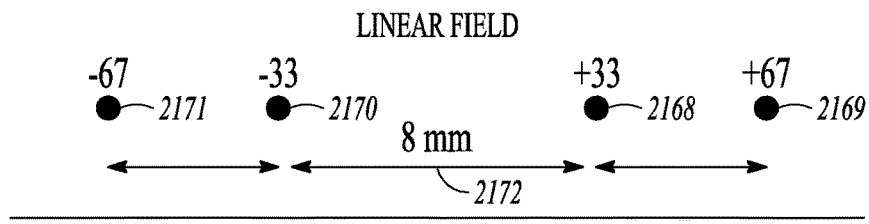
FIG. 21A illustrates an embodiment of to target multipole that includes fractionalized target anodes and fractionalized target cathodes.

More particularly, FIG. 21A illustrates an embodiment of a target multipole that includes fractionalized target anodes and fractionalized target cathodes designed to maximize the electric field in a region while minimizing the "activating function" (i.e. activation of dorsal columns, axons of passage) represented by the second difference of the extracellular potentials generated by a field. The target multipole illustrated in FIG. 21A progressively stacks fractionalization of target poles. The illustrated target multipole may be referred to as a base field design, as it may serve as a base from which the field length, width and orientation may be adjusted, and as a base from which features such as flanking electrodes may be added. In the illustrated embodiment, the target multipole includes first and second target anodes where in the first target anode 2168 represents 33% of the total anodic current and the second target anode 2169 represents 67% of the total anodic current; and further includes first and second target cathodes where in the first target cathode 2170 represents 33% of the total cathodic current and the second target anode 2171 represents 67% of the total cathodic current. Other percentages may be used to progressively increase the percentage moving away from the center of the target multipole and/or to alter the length of the target field. Some embodiments may include more than two target anodes in which the percentage of anodic current progressively increases away from the center of the target multipole. Some embodiments may include more than two target cathodes in which the percentage of cathodic current progressively increases away from the center of the target multipole. Some embodiments may include one target anode (100%) and more than one target cathode. Some embodiments may include one target cathode (100%) and more than one target anode.

Some embodiments of the target multipole may include a center 2172 of the target multipole, a first target anode 2168 and a second target anode 2169 on an anodic side of the center of the target multipole, and a first target cathode 2170 and a second target cathode 2171 on an opposing cathodic side of the center of the target multipole. The first and second target anodes, the center, and the first and second target cathodes may be in-line with each other. The first target anode and the first target cathode may have equal fractionalization magnitudes (e.g. 33% of the total anodic or cathodic current), and the second target anode and second target cathode may have equal fractionalization magnitudes (e.g. 67% of the total anodic or cathodic current). By way of example and not limitation, a shorter target multipole may have target poles with fractionalizations of 75/25/-25/-75 and a longer target multipole may have target poles with fractionalizations of 55/33/11/-11/-33/-55.

The distances from the first target anode to the center and from the first target cathode to the center may be equal. For example, the distance between the first target anode to the first target cathode is illustrated to be 8 mm. The distance between the first target anode to the center may be 4 mm, and the distance between the first target cathode to the center may be 4 mm. Similarly, distances from the second target anode to the center and from the second target cathode to the center may be equal (e.g. 8 mm). It is noted that the present subject matter may be implemented using other electrode spacings. Furthermore, if the spinal and electrode geometry are accounted for, the fractionalization magnitudes and the distances between the target poles may be unequal.

In some embodiments, the distances from the second target anode to the first target anode may be 4 mm, from the first target anode to the center may be 4 mm, from the center to the first target cathode may be 4 mm, and from the first target cathode to the second target cathode may be 4 mm. Thus, the distance of the second target cathode from the center may be twice the distance of the first target cathode form the center, and the distance of the second target anode from the center may be twice the distance of the first target anode from the center. The fractionalization magnitude of the second target cathode may be twice the fractionalization magnitude of the first target cathode, and the fractionalization magnitude of the second target anode may be twice the fractionalization magnitude of the first target anode.

Figure 21B:
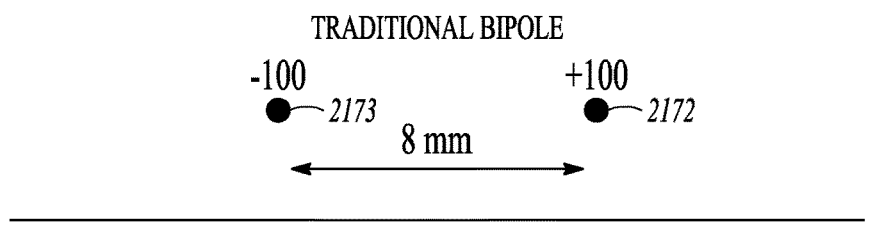
FIG. 21B illustrates a traditional bipole.
Figure 21C:
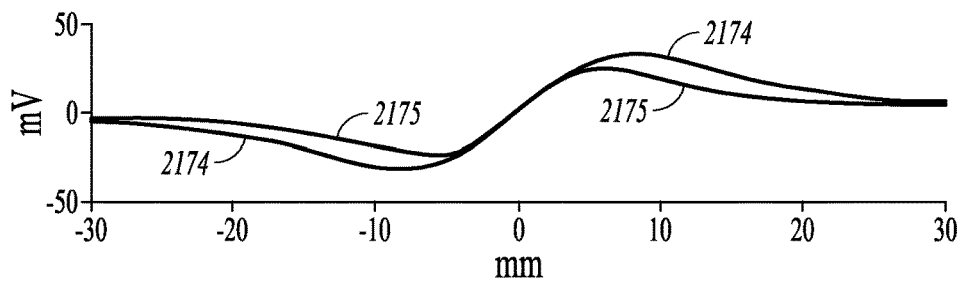
FIG. 21C compares a target multipole voltage and a bipole voltage.

The field design for the target multipole illustrated in FIG. 21A may be compared to a traditional bipole, illustrated in FIG. 21B, which has one anode 2172 and one cathode 2173. FIG. 21C compares a target multipole voltage 2174 in mV over the length of the base field design illustrated in FIG. 21A and a bipole voltage 2175 in mV over the length of the traditional bipole illustrated in FIG. 21B. As illustrated in FIG. 21C, the target multipole voltage 2174 has larger amplitude and a wider wave shape than the bipole voltage 2175.

Figure 21D:
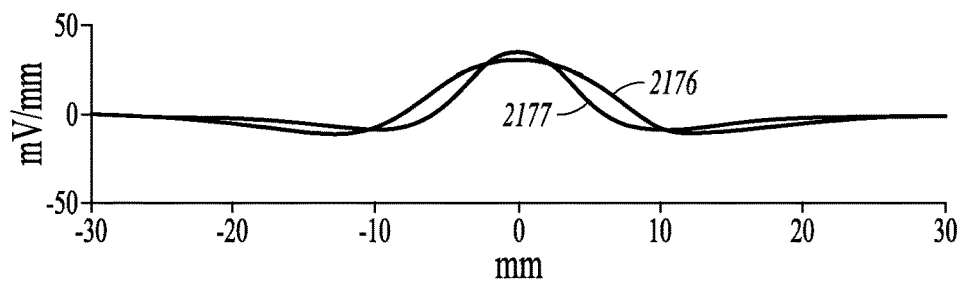
FIG. 21D compares a target multipole voltage per distance (electric field) and a bipole voltage per distance (electric field)

FIG. 21D compares a target multipole voltage per distance 2176 (first order spatial derivative of the voltage or "electric field") in mV per mm over the length of the base field design illustrated in FIG. 21A and a bipole voltage per distance 2177 (first order spatial derivative of the voltage or "electric field") in mV per mm over the length of the traditional bipole illustrated in FIG. 21B. As illustrated in FIG. 21D, the target multipole voltage per distance 2176 has only a slightly smaller peak voltage amplitude bipole voltage per distance 2177 but a wider field as it has a larger amplitude at −8 mm and 8 mm, for example. Thus, the base field design of FIG. 21A increases the electric field and the extent of the electric field in comparison to traditional bipole of FIG. 21B. As stated previously, DH fibers have an activating function proportional to the electric field, so it is desirable to increase the electric field and the extent of the electric field to modulate DH fibers.

Figure 21E:
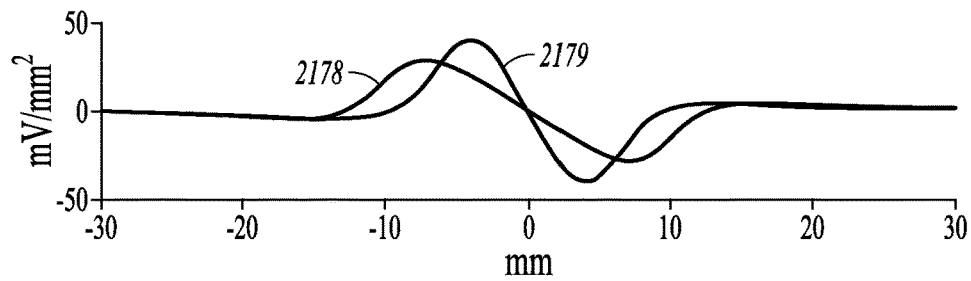
FIG. 21E compares a target multipole voltage per distance squared and a bipole voltage per distance squared (activating function).

FIG. 21E compares a target multipole voltage per distance squared 2178 (second order derivative of the voltage along the fiber axis) in mV per mm$^2$ for the base field design illustrated in FIG. 21A and a bipole voltage per distance squared 2179 (second order derivative of the voltage along the fiber axis) in mV per mm$^2$ for the traditional bipole illustrated in FIG. 21B. As illustrated in FIG. 21E, the target multipole voltage per distance squared 2178 has a smaller voltage amplitude bipole voltage per distance 2179 but also has a wider field. Thus, the base field design reduces the second order derivative of the voltage along the fiber axis. As stated previously, DC fibers have an activating function proportional to the second order derivative of the voltage along the fiber axis, so it is desirable to decrease the second order derivative of the voltage along the fiber axis to avoid modulation of DC fibers.

The field design may be applied to any frequency and to any amplitude. For example, the field design may be implemented for sub-perception modulation and may be implemented for supra-perception modulation.

Figure 22:
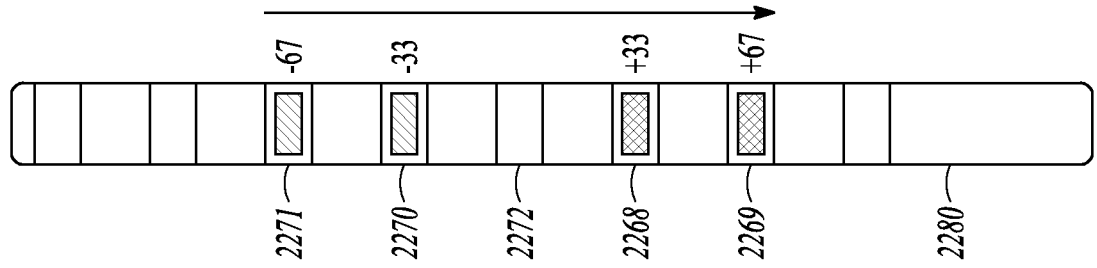
FIG. 22 illustrates, by way of example, a lead with a plurality of electrodes, and further illustrates the base field design, such as illustrated in FIG. 21A, implemented in the lead.

FIG. 22 illustrates a lead 2280 with a plurality of electrodes, and further illustrates the base field design, such as illustrated in FIG. 21A, implemented in the lead. The electrode 2272 at the center of the base field is not active, but the electrodes on each side of the electrode 2272 provide the first and second target anodes 2268 and 2269 and the first and second target cathodes 2270 and 2271. The progressive, monotonic fractionalizations (e.g. current amplitudes fractionalization) can be increasing or decreasing, and the field width may be longer or shorter. The weights for the base field may be equal or unequal so long as progression in the base field design is followed and/or the field is designed to maximize constant electric field over a region of spinal cord (dorsal column and dorsal horn). The base field design for the target multipole corresponds to the physical electrodes in this illustration.

The base field design may be implemented on any existing electrode design and/or combination of electrodes. The depictions provided herein represent examples, and are not intended to be an exhaustive depiction of all possible implementations of the base field.

Figure 23:
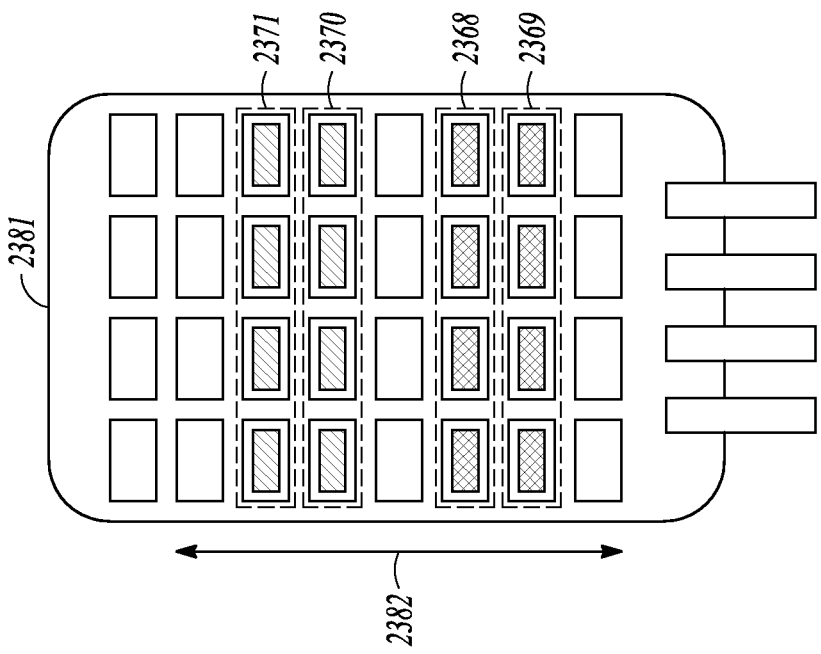
FIG. 23 illustrates, by way of example, a wider bipole field design, such as illustrated in FIG. 21A, implemented in a paddle lead.

FIG. 23 illustrates an example of widened base field design, such as illustrated in FIG. 21A, implemented in a paddle lead 2381. The orientation 2382 of the base field is aligned with the length of the paddle lead 2381, similar to the orientation of the field in the lead 22 illustrated in FIG. 22. Each of the first and second anodes 2368 and 2369, and the first and second cathodes 2370 and 2371 may be represented using one or more electrodes within a row of electrodes in the paddle.

Figure 24:
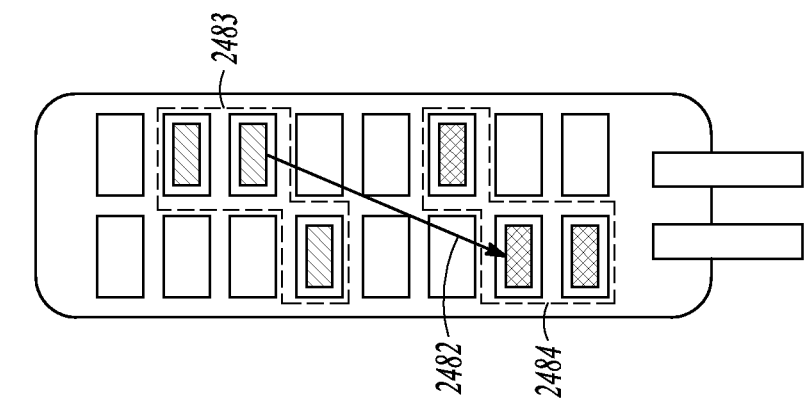
FIG. 24 illustrates, by way of example, the base field design in a paddle lead where the orientation of the base field is not aligned with the length of the paddle.

FIG. 24 illustrates an example of the base field design in a paddle lead where the orientation 2482 of the base field is not aligned with the length of the paddle. It is noted that the physical electrodes, including active cathodic electrodes 2483 and active anodic electrodes 2484 are illustrated in the figure rather than the rotated target multipole of the base field design. Thus, it is illustrated that the axis of linear progression need not be parallel to electrode alignment, which may be used to address angled placement and/or angled neurite and terminal track.

Figures 25, 26:
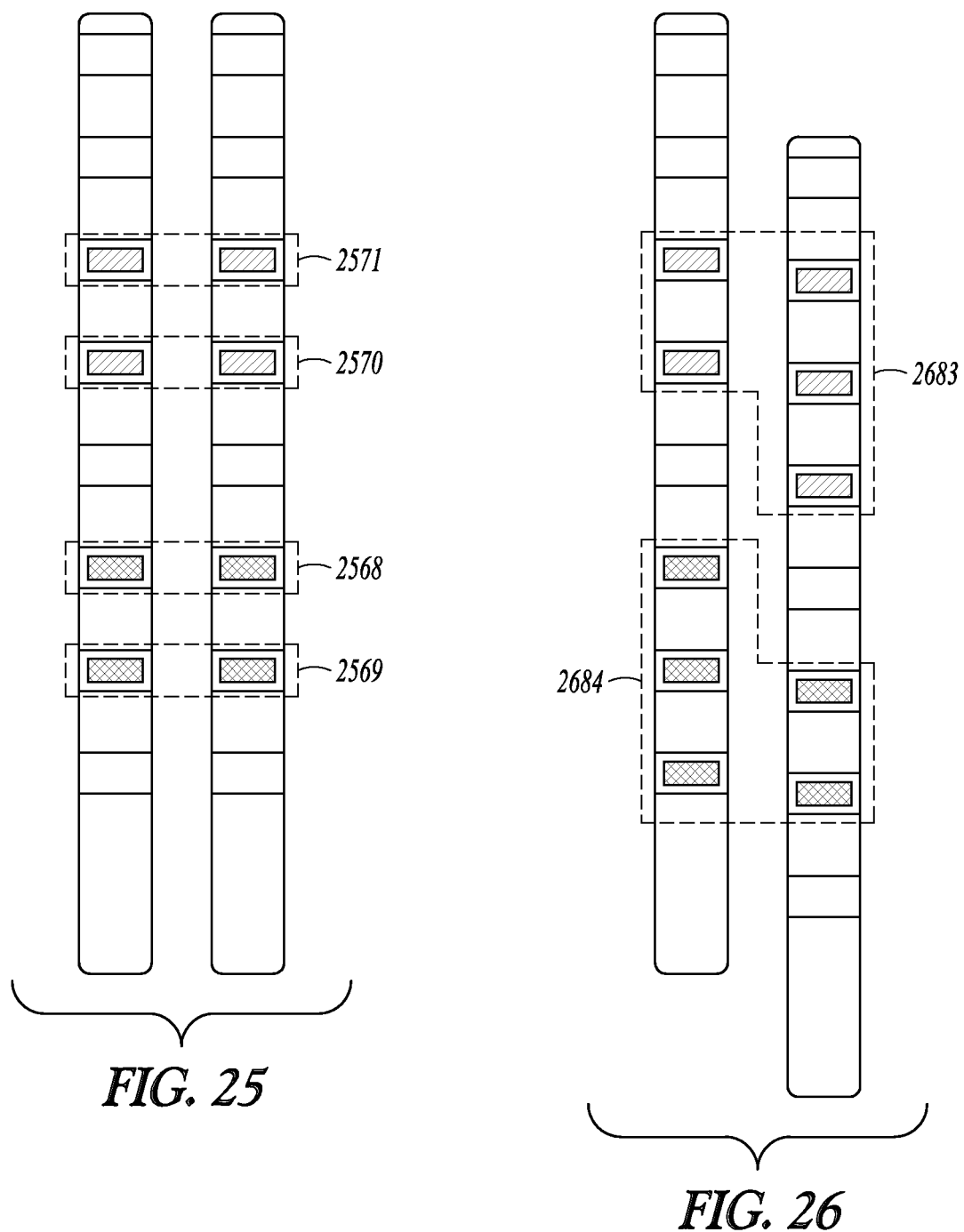
FIG. 25 illustrates, by way of example, the base field design, such as illustrated in FIG. 21A, implemented in a system that includes multiple leads.
FIG. 26 illustrates, by way of example, the base field, such as illustrated in FIG. 21A, in a system that includes staggered leads.

FIG. 25 illustrates an example of the base field design, such as illustrated in FIG. 21A, implemented in a system that includes multiple leads. Each lead may include a base field, such that the combination of leads provides a combined base field that is oriented in a direction generally aligned with the orientation of the leads. Similar to the paddle lead embodiment illustrated in FIG. 23, each of the first and second anodes 2568 and 2569, and the first and second cathodes 2570 and 2571 may be represented using rows of electrodes.

FIG. 26 illustrates an example of the base field, such as illustrated in FIG. 21A, in a system that includes staggered leads. Similar to the paddle lead embodiment illustrated in FIG. 24, the physical electrodes, including active cathodic electrodes 2683 and active anodic electrodes 2684 are illustrated in the figure rather than the target multipole of the base field design.

Various embodiments of the present subject matter provide a base field design interface and control. A paddle lead is used herein for purposes of illustration only. The present subject matter is not limited to implementations with paddle leads. For example, the present subject matter may be implemented with percutaneous leads and/or multiple leads.

FIG. 27 illustrates an example, using a paddle lead, where a central point of stimulation (e.g. A) is identified, and a linear field may be centered around the central point of stimulation. The centering of the linear field may be preprogrammed or may be calculated using a mathematical algorithm such as a forward/inverse solution paradigm. Multiple areas (e.g. "B") can be assigned simultaneously. Thus, in the illustrated example, there are a first target multipole 2785 and a second target multipole 2786 on the paddle lead. Each sweet spot can be tied to an "area" and linked to an independent timing source. Some embodiments may implement auto-controls, which may involve calculation of fields using offline software (e.g. COMSOL, MATLAB) and forward/inverse modeling to generate configuration that best matches target field specified/drawn by user.

FIG. 28 illustrates, by way of example and not limitation, advanced controls that may be implemented within a base field design interface. More advanced control allows the user to use settings in software suite (e.g. "Angle", "Focus", "Spread") to control angle orientation, vertical width, and horizontal width, respectively, of the linear field generated by the target multipole 2885 associated with the base field design. A paddle lead is illustrated with a central point of stimulation "A". Some interface embodiments provide an angle adjustment which can be controlled as illustrated at 2886 to allow a user to input an orientation for the base field design as illustrated at 2887. The angle adjustment could produce least-squares-error minimized fields that include more than two target anode and two target cathodes whose fractionalization assignments may differ from the base field embodiment with a fractionalization of 67/33/0/−33/−67 denoted earlier. Some interface embodiments provide a focus adjustment which can be controlled as illustrated at 2888 to change the distance of the target anode(s) and target cathode(s) from the central point of stimulation "A", which changes the extent of the electrical field along the orientation of the base field design as illustrated at 2289. Some interface embodiments provide a spread adjustment which can be controlled as illustrated at 2290, which changes the width or spread of the base field along a direction perpendicular to the orientation of the base field design as illustrated at 2291. The fractionalizations approximate the base field and may be pre-calculated for a given setting and/or calculated on-board. Some interface embodiments provide blended settings (e.g. angle+spread). Some interface embodiments provide an indication of the fractionalizations. Thus, the programming system may include a user interface configured to receive at least one user input selected from the group of user inputs consisting of a user input to adjust an angle of an axis of linear progression for the target multipole, a user input to adjust a focus of the target multipole to change a length of the linear electric field, and a user input to adjust a spread of the target multipole to change a width of the linear electric field.

Figure 29:
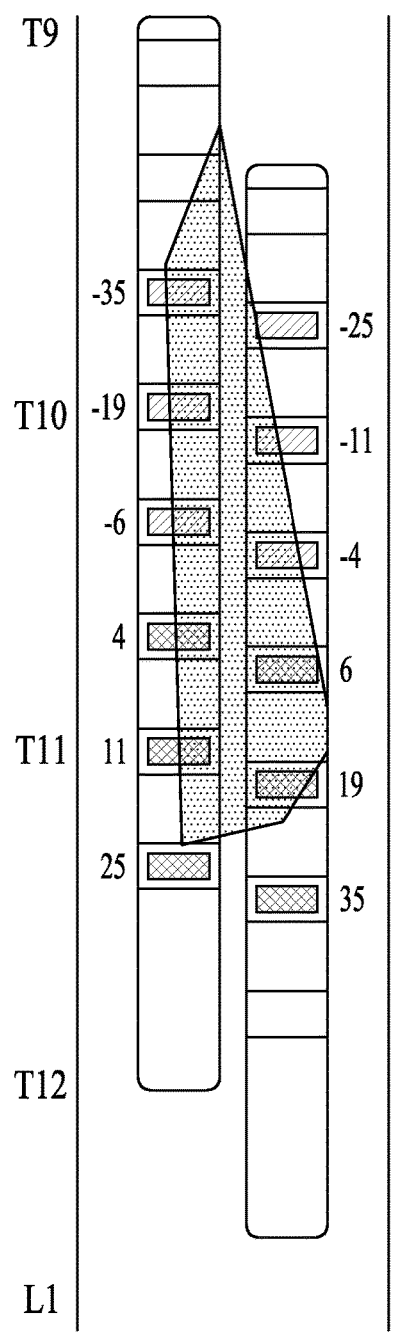
FIGS. 29-30 illustrate, by way of example and not limitation, an example of features of an interface to enable anatomical and patient-defined targeting.
Figure 30:
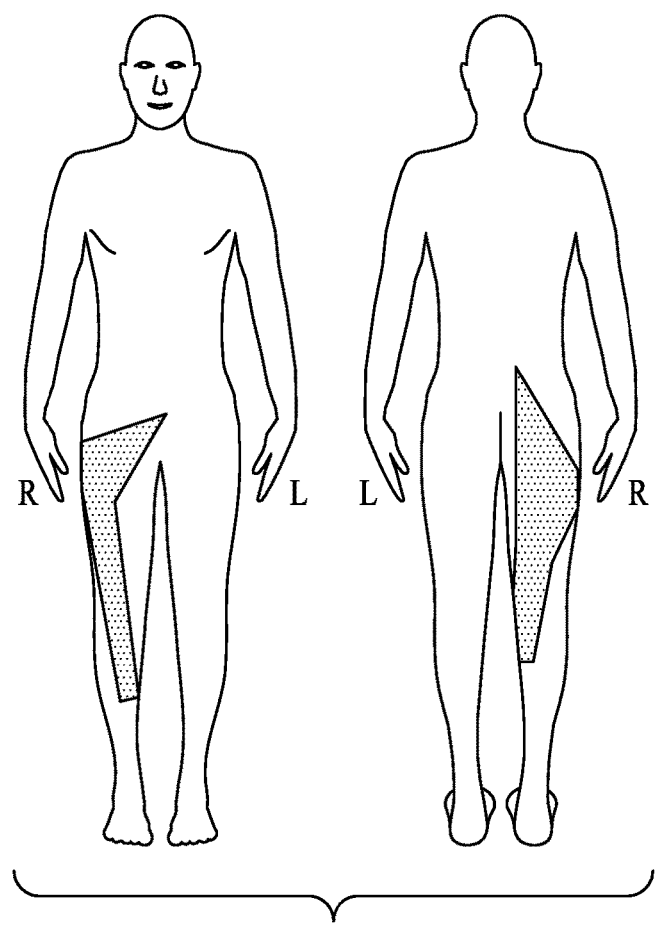
Figure 31:
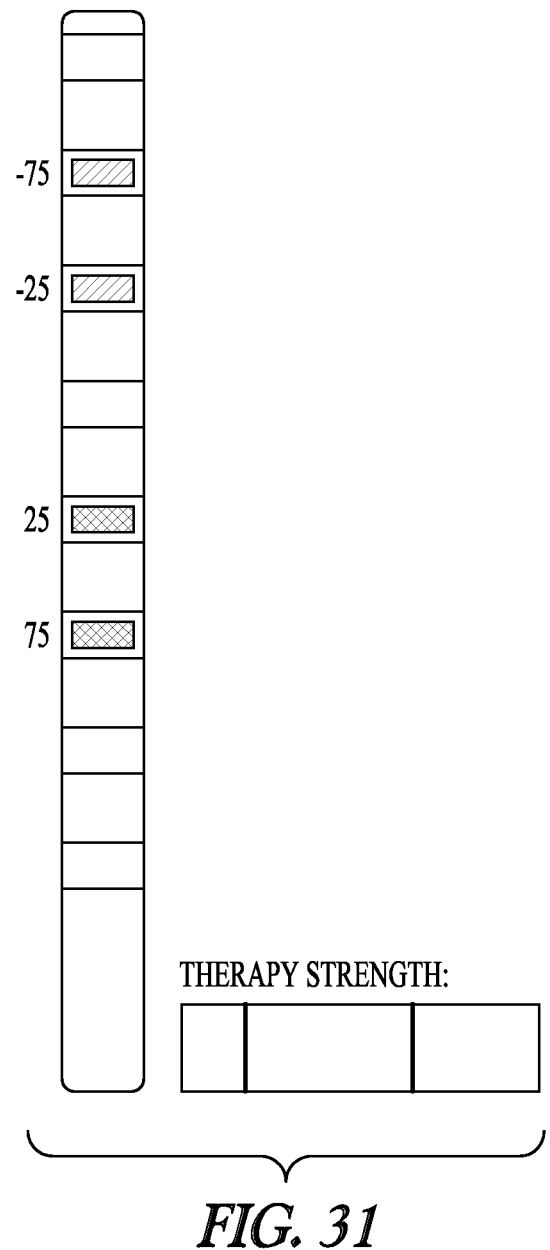
FIG. 31 illustrates, by way of example and not limitation, an example of features of an interface to implement a gradient control setting used to set the intensity of the modulation rather than set an absolute value of amplitude.

FIGS. 29-30 illustrate, by way of example and not limitation, an example of features of an interface to enable anatomical and patient-guided targeting. The anatomical target may be drawn, may be derived from a patient pain drawing via a look up table or an algorithm, or may be a combination thereof. FIG. 29 illustrates a region drawn over a representation of electrodes implanted in a patient. The system may use the drawing of the region to automatically or semi-automatically calculate the fractionalizations to provide a linear field that proximate the base field over the region. The programming system may be configured to receive as a user input a user-drawn region on an anatomical representation, and automatically determine the target multipole based on the user input. The target multipole may be used to determine the electrode fractionalizations for the plurality of electrodes. FIG. 30 illustrates a patient pain drawing which may serve as an input into the system for use in automatically or semi-automatically calculating the fractionalizations to provide a linear field to treat the pain in the identified regions. Spacial location(s) on the patient may be mapped to specific dermatomal levels of the spinal cord and specific medial-lateral locations at a given level. The mapping may be a point-by-point mapping via a look-up table or a dictionary/key system. The center, length, and width of the target linear field may be determined based on the spatial extent of the spinal cord region corresponding to the patient's reported pain region. A clinician or other specialist, a patient or a combination of persons may work together to highlight region of spinal cord and/or body where they want stimulation to be targeted (i.e. focus stimulation on anatomical correlate and/or reported site of pain). Internal look-up table and/or inverse algorithm with field "primitives" tied to specific regions/region sizes may be used to display and configure electrode settings according to this anatomically-based specification. The programming system may be configured to receive as a user input a user-identified patient pain areas, and automatically determining the target multipole based on the user input. The target multipole may be used to determine the electrode fractionalizations for the plurality of electrodes FIG. 31 illustrates, by way of example and not limitation, an example of features of an interface to implement a gradient control setting used to set the intensity of the modulation rather than set an absolute value of amplitude. Thus, for example, a patient or a clinician or other person may adjust a therapy strength by adjusting (e.g. drag-n-drop or arrows) a representation of the therapy strength. Instead of an explicit amplitude setting, a specialist may set strength of gradient and/or patient may set strength of therapy." As total current delivered is directly proportional to field strength, the actual stimulation amplitude in mA or V can be tied to specific points on the strength slider. This amplitude may or may not be displayed to the specialist/patient. For example, a therapy strength may correspond to a field strength of 10 mV/mm, and an amplitude may be set to 1.7 mA. Should the therapy be adjusted to a field strength of 40 mV/mm, the amplitude may be set proportionally (e.g. 6.8 mA). Amplitude may then be de-coupled from field strength, as different configurations may require different amplitudes to achieve same field strength.

Figure 32:
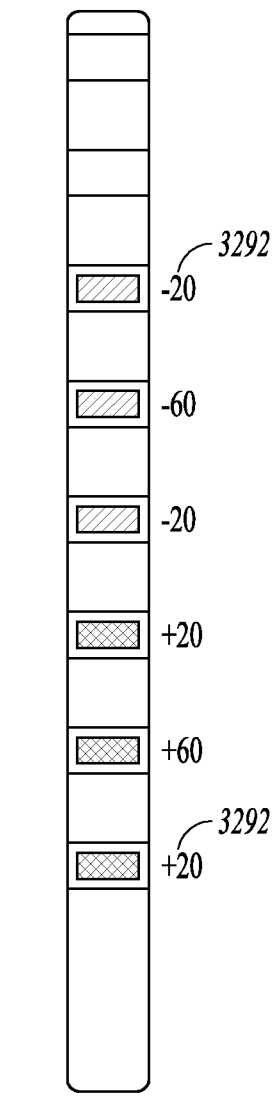
FIG. 32 illustrates, by way of example, edge guarding including use flanking electrodes to dampen Ve differences at edges of active electrodes.

FIG. 32 illustrates, by way of example, edge guarding including use flanking electrodes 3292 to dampen Ve differences at edges of active electrodes. Some embodiments may use edge guarding to increase the threshold required for paresthesias, thus reducing the likelihood and severity of sensory side effects. This feature may be toggled as an option on programming screen or with an interface icon, feature, slider, and the like.

Figure 33:
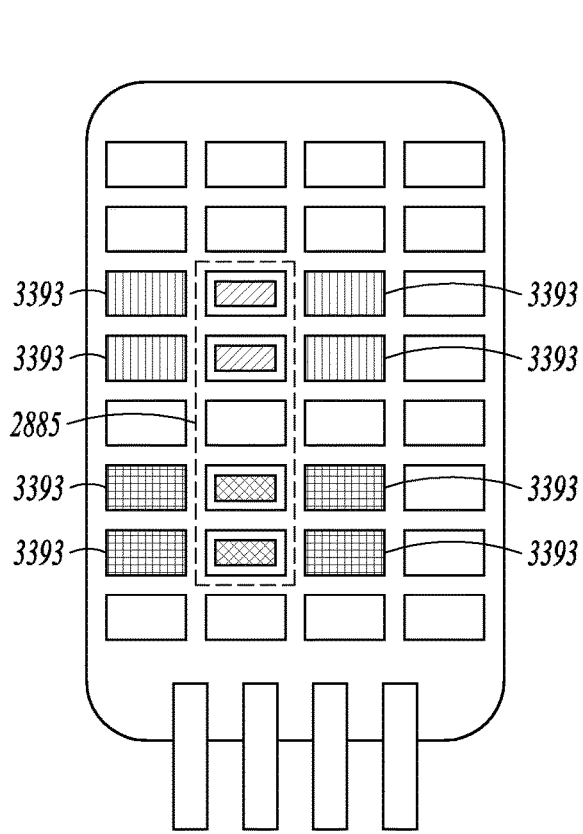
FIG. 33 illustrates, by way of example, current steering including use of flanking electrodes on each side of each target anode and target cathode in the target multipole.

FIG. 33 illustrates, by way of example, current steering including use of flanking electrodes 3393 on each side of each target anode and target cathode in the target multipole. The primary linear field flanked by smaller amplitude linear fields intended to "guard" the central field and steer current into the specific region(s) of the spinal cord where stimulation is needed. Guarding fields are opposite the polarity of the main field and/or are derived from a mathematical algorithm to minimize stimulation of neural elements outside of the target region. This feature may be toggled as an option on programming screen or with an interface icon, feature, slider, and the like.

Figure 34:
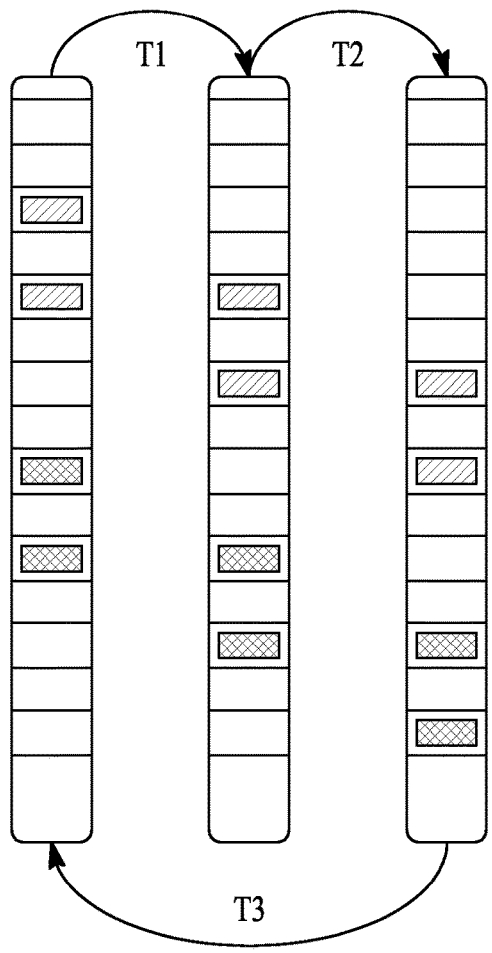
FIG. 34 illustrates, by way of example and not limitation, an automatic or semiautomatic movement of the target multipole along the lead.

FIG. 34 illustrates, by way of example and not limitation, an automatic or semiautomatic movement of the target multipole along the lead. The motion may be cyclical, as represented by T1, T2, and T3. Some embodiments may implement a rolling electrical field, which may be programmed to move up and down the lead(s) at pre-determined and/or random time intervals e.g. to increase spinal cord coverage or to support different use cases. Multiple settings may also be cycled through one field, or a mix of these configurations may exist. Thus, the neural modulation generator is programmed to automatically move the target multipole within an array of electrodes. This feature may be toggled as an option on programming screen or with an interface icon, feature, slider, and the like.

Search heuristics may be used to generate fields. In an embodiment, the efficacy is proportional to the maximum absolute value for the electrical field max(abs(E)) where the number of poles is fixed. Some embodiments may fix the polarity of poles, and some embodiments may allow the polarity of poles to change.

Some embodiments may implement search heuristics with some constraints (e.g. minimum distance between poles, maximum charge/current on each pole), and determine the optimized distance and amplitude on each pole to achieve a maximum electric field through an iterative process and in patient-specific manner. Some embodiments may integrate with imaging.

Some embodiments may implement a more complex embodiment that implements search heuristics. The number of poles may be optimized and controlled for orientation or an adjusted width or length. A negative cost function may be added for other activation terms (e.g. of dorsal columns, terminals perpendicular to E-field direction).

Configurations shown above may be specifically designed to target specific mechanisms of action pertaining to (subperception) SCS and optimized as such. However, the present subject matter involves the family of fields generated from this optimization and ways to program, configure, and further optimize (e.g. in a patient-specific manner) the proposed fields.

Features in this field may or may not be optimized due to technical constraints and/or to minimize side effects. For example, edge guarding or current steering may be optimized. The "roll off" at the ends of the field may be optimized to prevent excessive jump in activating function/field. The limitation(s) on slope of the field may be optimized to prevent activation of other, unwanted terminals (e.g. those from excitatory and pronociceptive neurons). Some systems may optimize limitation(s) on slope, amplitude, distance between active contacts for purpose of conserving energy (e.g. distribute fields in such a way as to minimize battery drain, as bipoles cancel and require more offset).

Some embodiments may optimize the base field based on clinical effects. Additionally or alternatively, the target gradient field, amplitude of slope, angle of field, and width of field may be optimized according to patient preference/choice through a connected a patient registry, an internal algorithm on the CP, and the like.

Figure 35:
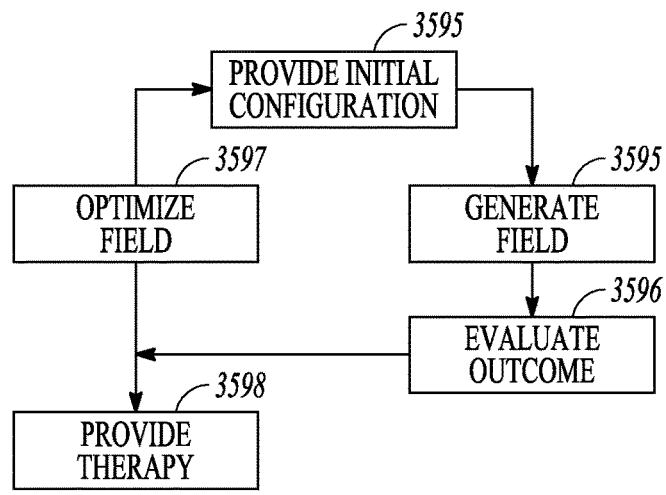
FIG. 35 provides an example of a system flow that may be implemented to optimize a field.

FIG. 35 provides an example of a system flow that may be implemented to optimize a field. This may be performed off-line, and the final field configurations/settings uploaded to the programming device, or if the algorithm is computationally efficient enough, this may be performed on-board the stimulation programmer/remote/app.

At 3594, a configuration is initially provided. The configuration may be randomly generated using previously described constraints (e.g. the number of active contacts, width, focus, angle, and the like). The configuration may be initialized with an estimate. At 3595, the field may be generated by a configuration calculated using analytical solutions and/or derived from a clinical outcome if applied to the patient.

At 3596, the outcome measure for the field evaluated using the optimization score based on factors. Factors that may be weighted may include field attributes. An example is $\alpha$ x electric field strength $-\beta$ x side effect (e.g. activation function, paresthesia) $-\delta$ x difference in area vs patent specification. Specific mechanisms (e.g. presynaptic terminal activation assessed using specific computational and/or pre-clinical models (e.g. in NEURON, MATLAB), and/or patient reports. More or fewer terms like $\alpha$, $\beta$ and $\delta$.

At 3597, fields sorted by an optimization algorithm or algorithms may be recombined using choice of search heuristic (e.g. genetic algorithm, simulated annealing, gradient descent) to become more optimal, with features providing a higher optimization score emphasized in future generations over features that produce lower optimization scores.

At 3598, the fields may be given to the patient based upon patient preference or specified acceptance criteria. Field features may be inputted into an optimization function. Multiple fields may be saved into program cycling feature.

FIGS. 36A-38H illustrate, by way of example and not limitation, some addition examples of target multipoles that progressively stack fractionalization of target poles in a directional, progressive manner to produce a linear field. Each of these figures also illustrate some physical electrodes used to produce the fractionalized poles. FIGS. 36A-36F illustrate 12 mm electrode spacing, FIGS. 37A-37F illustrate 16 mm electrode spacing, and FIGS. 38A-38H illustrate 20 mm electrode spacing.

FIGS. 36A-36F generally illustrate the same target multipole with first and second target anodes and first and second target cathodes. The second target anode is larger than the first target anode, and the second target cathode is larger than the first target cathode. The fractionalized current delivered to the underlying physical electrodes may be adjusted to move the target multipole, by way of example and not limitation, to be centered laterally on the left column of electrodes with the target poles centered longitudinally at 25% from the electrode top (FIG. 36A), to be centered laterally on the left column of electrodes with the target poles centered longitudinally between rows in the left column of electrodes (FIG. 36B), to be centered laterally on the left column of electrodes with the target poles centered longitudinally on electrodes in the left column of electrodes (FIG. 36C), to be centered laterally on a midline between the columns and centered longitudinally with the electrode rows (FIG. 36D), to be centered laterally on a midline between the columns with the target poles centered longitudinally at 25% from the electrode row top (FIG. 36E), and to be centered laterally on a midline between the columns with the target poles centered longitudinally between rows of electrodes (FIG. 36F).

Figures 37A, 37B, 37C, 37D, 37E, 37F:
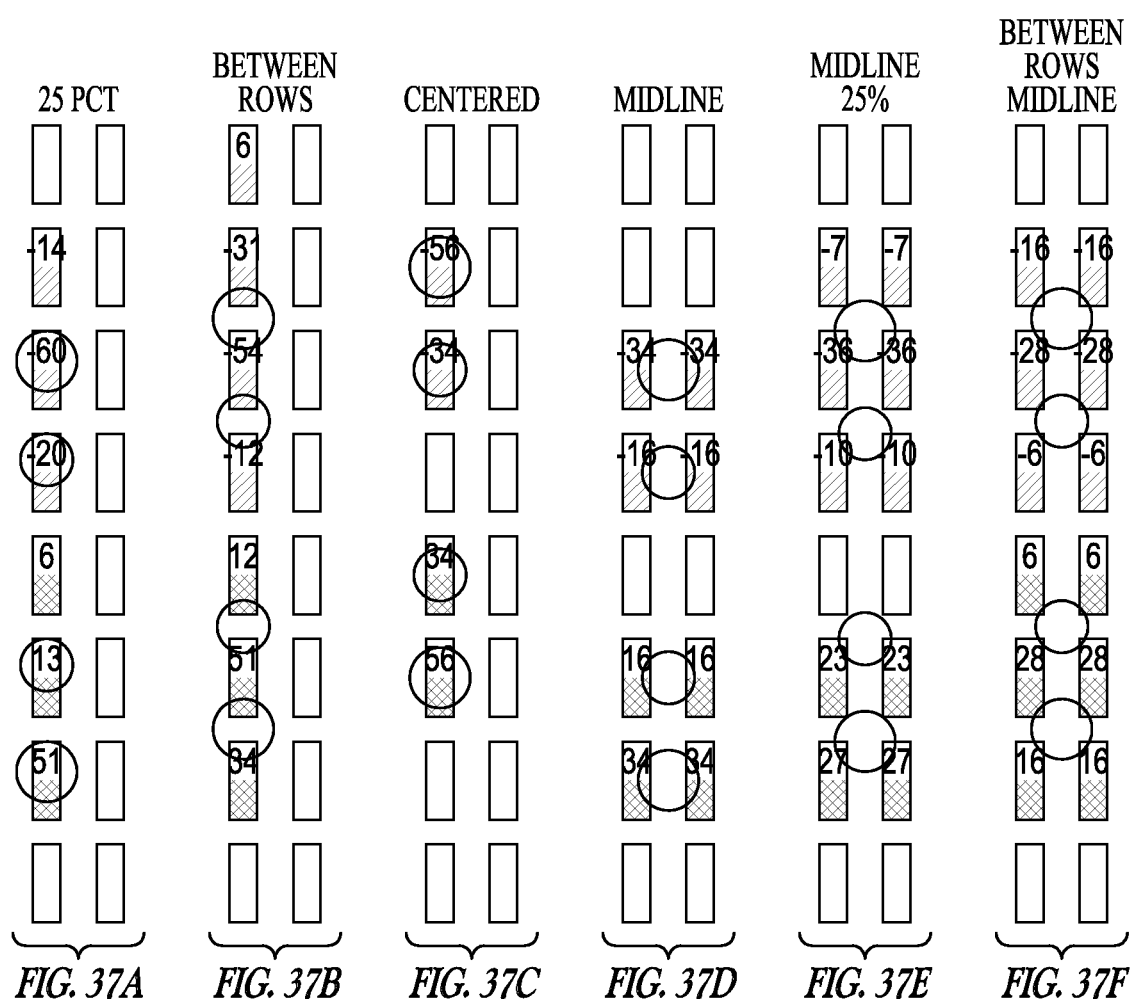

FIGS. 37A-37F generally illustrate the same target multipole with first and second target anodes and first and second target cathodes. The second target anode is larger than the first target anode, and the second target cathode is larger than the first target cathode. The fractionalized current delivered to the underlying physical electrodes may be adjusted to move the target multipole, by way of example and not limitation, to be centered laterally on the left column of electrodes with the target poles centered longitudinally at 25% from the electrode top (FIG. 37A), to be centered laterally on the left column of electrodes with the target poles centered longitudinally between rows in the left column of electrodes (FIG. 37B), to be centered laterally on the left column of electrodes with the target poles centered longitudinally on electrodes in the left column of electrodes (FIG. 37C), to be centered laterally on a midline between the columns and centered longitudinally with the electrode rows (FIG. 37D), to be centered laterally on a midline between the columns with the target poles centered longitudinally at 25% from the electrode row top (FIG. 37E), and to be centered laterally on a midline between the columns with the target poles centered longitudinally between rows of electrodes (FIG. 37F).

FIGS. 38A-38H generally illustrate the same target multiple with first and second target anodes and first and second target cathodes. The second target anode is larger than the first target anode, and the second target cathode is larger than the first target cathode. The fractionalized current delivered to the underlying physical electrodes may be adjusted to move the target multipole, by way of example and not limitation, to be centered laterally on the left column of electrodes with the target poles centered longitudinally at 25% from the electrode top (FIG. 38A), to be centered laterally on a midline between the columns with the target poles centered longitudinally at 25% from the electrode row top (FIG. 38B), to be centered laterally on the left column of electrodes with the target poles centered longitudinally at 75% from the electrode top in the left column of electrodes (FIG. 38C), to be centered laterally on a midline between the columns with the target poles centered longitudinally at 75% from the electrode row top (FIG. 38D), to be centered laterally on the left column of electrodes with the target poles centered longitudinally between rows in the left column of electrodes (FIG. 38E), to be centered laterally on a midline between the columns with the target poles centered longitudinally between rows in the left column of electrodes (FIG. 38F), to be centered laterally on the left column of electrodes with the target poles centered on electrodes in the left column of electrodes (FIG. 38G), to be centered laterally on a midline between the columns with the target poles centered longitudinally on electrode rows (FIG. 38H).

The above detailed description is intended to be illustrative, and not restrictive. The scope of the disclosure should, therefore, be determined with references to the appended claims, along with the full scope of equivalents to which such claims are entitled.

What is claimed is:

1. A method for modulating a volume of tissue using a plurality of electrodes, comprising:
   programming a modulation parameter set, including determining electrode fractionalizations for the plurality of electrodes based on a target multipole having at least three target poles, wherein the programmed parameter set includes the determined electrode fractionalizations, and the target multipole directionally and- progressively increases fractionalization magnitudes of target poles from a point within the target multipole to provide a linear electric field over the volume of tissue; and
   delivering energy using the active physical electrodes and the programmed parameter set to provide the linear electric field.

2. The method of claim 1, wherein the target multipole includes:
   a center;
   a first target anode and a second target anode on an anodic side of the center of the target multipole; and
   a first target cathode and a second target cathode on an opposing cathodic side of the center of the target multipole.

3. The method of claim 2, wherein the target multipole further comprises a flanking target anode on the anodic side of the center, and a flanking target cathode on the cathodic side of the center, wherein the first, second and flanking target anodes, the center, and the first, second and flanking target cathodes are in-line.

4. The method of claim 1, wherein the at least three target poles are in-line with each other.

5. The method of claim 4, wherein the first target anode and the first target cathode have equal fractionalization magnitudes, and the second target anode and second target cathode have equal fractionalization magnitudes.

6. The method of claim 5, wherein distances from the first target anode to the center and from the first target cathode to the center are equal, and distances from the second target anode to the center and from the second target cathode to the center are equal.

7. The method of claim 6, wherein the distances from the second target anode to the first target anode, from the first target anode to the center, from the center to the first target cathode, and from the first target cathode to the second target cathode are equal.

8. The method of claim 1, wherein the target multipole, which directionally and progressively increases fractionalization magnitudes of target poles, includes:
   a center;
   a first target anode separated from the center;
   a second target anode separated from the first target anode, wherein the second target anode is further away from the center than the first target anode and the second target anode has a higher fractionalization percentage then the first target anode;
   a first target cathode separated from the center; and
   a second target cathode separated from the first target cathode wherein the second target cathode is further away from the center than the first target cathode and the second target cathode has a higher fractionalization percentage then the first target cathode.

9. The method of claim 8, wherein the target multipole, which directionally and progressively increases fractionalization magnitudes of target poles, includes a third target anode on the anodic side of the center of the target multipole and a third target cathode on the cathodic side of the center of the target multipole.

10. The method of claim 8, wherein the target multipole further comprises a flanking target anode separated from the second target anode by the length, and a flanking target cathode separated from the second target cathode by the length.

11. The method of claim 8, wherein the target multipole further comprises flanking electrodes on opposing sides of the first target anode and having opposite polarity to the first target anode, flanking electrodes on opposing sides of the second target anode and having opposite polarity to the second target anode, flanking electrodes on opposing side of the first target cathode and having opposite polarity to the first target cathode, and flanking electrodes on opposing sides of the second target cathode and having opposite polarity to the second target cathode.

12. The method of claim 1, further comprising receiving a user input to adjust an angle of an axis of linear progression for the target multipole.

13. The method of claim 1, further comprising receiving a user input to adjust a focus of the target multipole to change a length of the linear electric field.

14. The method of claim 1, further comprising receiving a user input to adjust a spread of the target multipole to change a width of the linear electric field.

15. The method of claim 1, further comprising receiving as a user input a user-drawn region on an anatomical representation, automatically determining the target multipole based on the user input, the target multipole being used to determine the electrode fractionalizations for the plurality of electrodes.

16. The method of claim 1, further comprising receiving as a user input a user-identified patient pain area, automatically determining the target multipole based on the user input, the target multipole being used to determine the electrode fractionalizations for the plurality of electrodes.

17. The method of claim 1, further comprising displaying a gradient control element on a user interface, receiving a user input to adjust the gradient control element that is displayed on the user interface, and adjusting a strength of a therapy based on the adjusted gradient control element.

18. The method of claim 1, further comprising automatically moving the target multipole within an array of electrodes.

19. The method of claim 1, further comprising implementing a search heuristic to optimize a distance between poles in the target multipole and a current amplitude on each pole in the target multipole to maximize an absolute value of the electric field.

20. The method of claim 19, further comprising implementing the search heuristic to optimize for a number of poles in the target multipole, orientation angle of the electric field, focus of the electric field, and spread of the electric field.

* * * * *